United States Patent
Savonnet et al.

(10) Patent No.: US 11,384,195 B2
(45) Date of Patent: Jul. 12, 2022

(54) DIFUNCTIONAL BIPHENYL COMPOUNDS, PREPARATION, AND USES

(71) Applicants: ARIANEGROUP SAS, Paris (FR); CENTRE NATIONAL DE LA RECHERCHE SCIENTIFIQUE, Paris (FR)

(72) Inventors: Etienne Savonnet, Bordeaux (FR); Brigitte Defoort, Saint-Medard-en-Jalles (FR); Henri Cramail, Sainte-Terre (FR); Stéphane Grelier, Parentis-en-Born (FR); Etienne Grau, Bordeaux (FR)

(73) Assignees: ARIANEGROUP SAS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 115 days.

(21) Appl. No.: 16/968,474

(22) PCT Filed: Feb. 7, 2019

(86) PCT No.: PCT/FR2019/050273
§ 371 (c)(1),
(2) Date: Aug. 7, 2020

(87) PCT Pub. No.: WO2019/155169
PCT Pub. Date: Aug. 15, 2019

(65) Prior Publication Data
US 2020/0399419 A1 Dec. 24, 2020

(30) Foreign Application Priority Data
Feb. 8, 2018 (FR) .................................... 1851071

(51) Int. Cl.
| | | |
|---|---|---|
| *C08G 18/76* | (2006.01) | |
| *C07C 217/58* | (2006.01) | |
| *C07C 217/84* | (2006.01) | |
| *C07C 265/12* | (2006.01) | |
| *C08G 59/32* | (2006.01) | |

(52) U.S. Cl.
CPC ........ *C08G 18/7685* (2013.01); *C07C 217/58* (2013.01); *C07C 217/84* (2013.01); *C07C 265/12* (2013.01); *C08G 59/32* (2013.01)

(58) Field of Classification Search
CPC ... C07C 217/58; C07C 217/84; C07C 247/24; C07C 251/48; C07C 265/12; C07C 265/14; C08G 18/7685; C08G 59/32; C08G 59/50
See application file for complete search history.

(56) References Cited

FOREIGN PATENT DOCUMENTS

| | | |
|---|---|---|
| EP | 0 352 775 A1 | 1/1990 |
| EP | 3 002 333 A1 | 4/2016 |
| FR | 2 734 832 A1 | 12/1996 |

OTHER PUBLICATIONS

Chapman, et al., "Studies related to the Chemistry of Melanins . . . ", Journal of the Chemical Society C: Organic, vol. 1970, No. 6, pp. 865-972 (Year: 1970).*
International Search Report as isssued in the International Patent Application No. PCT/FR2019/050273, dated Jun. 14, 2019.
Fache, M., et al., "Vanillin production from lignin and its use as a renewable chemical," ACS: Sustainable Chemistry & Engineering, Dec. 2015, 24 pages.
Fache, M., et al., "Amine hardeners and epoxy cross-linker from aromatic renewable resources," European Polymer Journal, vol. 73, (2015), pp. 344-362.
Gaur, M., et al., "Improved device performance based on crosslinking of poly (3-hexylthiophene," Synthetic Metals, vol. 160, No. 19-20, Oct. 2010, XP027380392, pp. 2061-2064.
Chapman, R. F., et al., "Studies related to the Chemistry of Melanins. Part VII. Attmepts to Synthesise Hydroxlated Bi-indolyls, Biphenyls, and Indoline-2-carboxylic Acid as Possible Intermediates in the Formation of Melanins from 3,4-Dihydroxyphenethylamine and 3,4-Dihydroxyphenylalanine," Journal of the Chemical Society C: Organic, vol. 1970, No. 6, Jan. 1970, XP055195932, pp. 865-972.
Llevot, A., et al., "Renewable (semi)aromatic polyester from symmetrical vanillin-based dimers," Polymer Chemistry, vol. 6, No. 33, Jul. 2015, pp. 6058-6066.
Kurt Maurer, V., et al., "New derivatives of dihydro-divanillin and experience of the catalytic Reduction of nitrostyrenes," Journal fur Praktische Chemie: Pratical Applications and Applied Chemistry: Covering all Aspects of Applied Chemistry, vol. 144, No. 1-2, Oct. 1935, XP0555526673, 9 pages.

\* cited by examiner

*Primary Examiner* — Yevgeny Valenrod
*Assistant Examiner* — Blaine G Doletski
(74) *Attorney, Agent, or Firm* — Pillsbury Winthrop Shaw Pittman LLP

(57) ABSTRACT

A difunctional biphenyl compounds corresponding to formula (I)

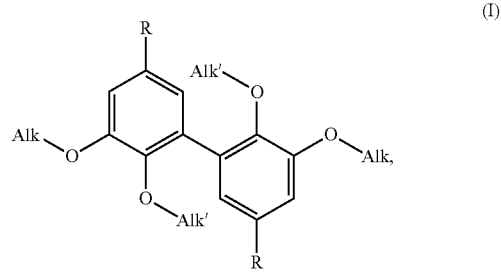

wherein Alk, Alk' and R are as defined in the description. These compounds are suitable as hardeners for thermosetting resins, especially epoxy resins.

16 Claims, 17 Drawing Sheets

DIFUNCTIONAL BIPHENYL COMPOUNDS, PREPARATION, AND USES

CROSS-REFERENCE TO RELATED APPLICATIONS

This application is the U.S. National Stage of PCT/FR2019/050273, filed Feb. 7, 2019, which in turn claims priority to French patent application number 1851071 filed Feb. 8, 2018. The content of these applications are incorporated herein by reference in their entireties.

The main object of the present invention is difunctional biphenyl compounds, i.e. biphenyl compounds with two reactive functions. Said two reactive functions are of the methylamino, isocyanate or amino type (see formula (I) given below). These compounds are particularly suitable as curing agents (cross-linking polymerization agents or difunctional crosslinking agents, due to the presence of the two reactive functions in their formula), of thermosetting monomers or prepolymers, in particular:

- in a context of reactive functions with an amino group (of the methylamino or amino type), of thermosetting monomers or prepolymers of the epoxy resin type (with epoxy functions), polycarbonate (with carbonate functions) and polycarboxylic acid type (with carboxylic acid functions) to, respectively, obtain polyepoxides, poly(hydroxy)urethanes (NiPU: non-isocyanate polyurethane) and polyamides; and
- in a context of reactive functions with an isocyanate group (reactive functions of the isocyanate type), of thermosetting monomers or prepolymers of the polyol resin and polyamine resin type to, respectively, obtain polyurethanes and polyamides.

These compounds are of particular interest in that they are perfectly suitable for obtaining products (such as thermosetting monomers or thermosetting prepolymers) with high mechanical and temperature resistance properties (suitable for numerous applications, particularly in the field of adhesives and composites) and in that, for many of them, they can be obtained, in addition to by conventional synthesis routes (known in the field of petrochemistry), from biomass (from lignin, more precisely from vanillin) (referred to as biosourced compounds).

The present invention also has as its object the preparation of said difunctional biphenyl compounds and their uses.

To date:

particularly for the crosslinking polymerization of epoxy resins, especially for the crosslinking polymerization of the most used ones, obtained from the monomer (n=0 (see formula below)) or prepolymer (n≠0 (see formula below)) diglycidyl ether of bisphenol-A (DGEBA), which has the following formula:

conventional hardeners with amine-type (reactive) functions are mostly used. These include, but are by no means limited to, diaminodiphenyl sulfone (DDS), diaminodiphenylmethane ((DDM) or methylene dianiline (MDA)), isophorone diamine (IPDA), dicyandiamide, 4,4-methylene-bis(2-isopropyl-6-methylaniline) (notably marketed by Lonza Ltd under the trade name Lonzacure® M-MIPA), and 4,4'-methylene-bis(2,6-diisopropylamineaniline) (marketed by Lonza Ltd under the trade name Lonzacure® M-DIPA). For convenience, the formulas of the first two conventional hardeners of the prior art identified in the above list are shown below:

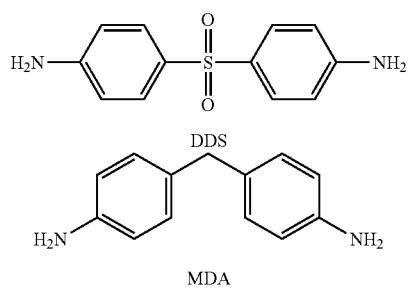

Incidentally, alcohols, carboxylic acids, anhydrides, thiols and even isocyanates (all of which are difunctional) can and are also used as hardeners for epoxy resins.

To date, little work has been done to find alternative compounds to conventional hardeners, especially biosourced alternative compounds. Fache et al. were interested in vanillin, whose chemical formula is reproduced below for all intents and purposes:

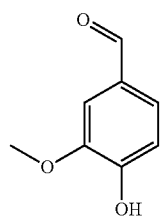

and proposed, in *European Polymer Journal*, 2015, 73, 344-362, as a bio-sourced alternative compound to conventional epoxy resin hardeners, vanillylamine (synthesized, via vanillyloxime, from said vanillin). Said vanillylamine, therefore used as a hardener for thermosetting epoxy monomers or prepolymers, does not allow the production of polyepoxides which have high mechanical and temperature resistance properties.

In such a context, it is to the inventors' credit that they have proposed novel difunctional biphenyl compounds (suitable as hardeners (see above and below)), many of

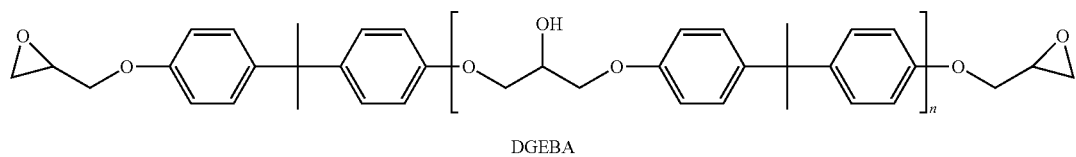

DGEBA which may be of natural origin). Said novel difunctional biphenyl compounds correspond to formula (I) below:

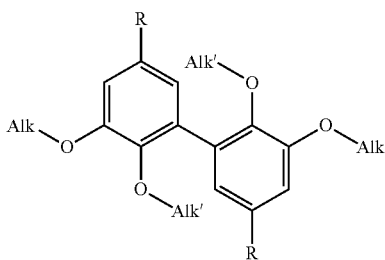

wherein:
Alk is a linear or branched alkyl group having from 1 to 6 carbon atoms,
Alk' is a linear or branched alkyl group having from 1 to 6 carbon atoms, and
R is selected from —CH$_2$—NH$_2$, —N=C=O and —NH$_2$.

Formula (I) above confirms that the compounds of the invention are difunctional biphenyl compounds, difunctional due to the presence of the two (identical) R groups. Said two R groups are selected from the aminomethyl groups (—CH$_2$—NH$_2$), isocyanate (—N=C=O) and amino (—NH$_2$). It is understood that these R groups are suitable for reaction with thermosetting monomers or prepolymers, in particular as identified above.

R, amino group (directly carried by the phenyl nuclei), is particularly preferred.

As regards the alkoxy group, —O-Alk, as defined above (Alk=linear or branched alkyl group having from 1 to 6 carbon atoms), it advantageously consists of an alkoxy group, —O-Alk$_{lower}$, said lower alkyl group having only 1 to 4 carbon atoms, or very advantageously only 1 or 2 carbon atoms. It will be understood below that the value of Alk is determined by the nature of the starting materials used. Thus, from synthetic ethyl vanillin, compounds of formula (I) are obtained in which Alk=—C$_2$H$_5$ (more generally, from synthetic (C$_2$-C$_6$)alkyl vanillin, compounds of formula (I) are obtained in which Alk is a C$_2$-C$_6$ alkyl group), from vanillin (synthetic or, rather advantageously, of natural origin), compounds of formula (I) are obtained in which Alk=—CH$_3$. Said compounds of formula (I) in which Alk=—CH$_3$ (Alk is a methyl group) are particularly preferred (in particular because they can be obtained from natural vanillin and with reference to their viscosities). Thus, the rest of the present description and the examples are extensively developed, in no limiting way, with reference to this preferred value.

With regard to the alkoxy group, —O-Alk', as defined above (Alk'=linear or branched alkyl group having from 1 to 6 carbon atoms), it also advantageously consists of an alkoxy group, —O-Alk'$_{lower}$, said lower alkyl group having only 1 to 4 carbon atoms, or very advantageously only 1 or 2 carbon atoms. It will be understood below that the value of Alk' is controlled by the exact nature of the iodoalkane used for alkylating (etherifying the hydroxy functions in the 4,4' position of the dimer). Compounds of formula (I) in which Alk'=—CH$_3$ (Alk' is a methyl group) are particularly preferred (especially with reference to their viscosities).

It has been understood that Alk and Alk' are independent (which is confirmed below when considering the process of preparation of the compounds of the invention), that they are therefore by no means necessarily identical. However, in the context of a particularly preferred variant, Alk=Alk'=—CH$_3$ (=a methyl group).

Thus, particularly preferred are compounds of the formula (I) wherein:
Alk=Alk'=—CH$_3$ and R=—CH$_2$—NH$_2$, i.e. 3,4-dimethoxydivanyllylamine (see Example 1 below),
Alk=Alk'=—CH$_3$ and R=—N=C=O, i.e. 3,4-dimethoxydiphenylisocyanate (see Example 2 below), and
Alk=Alk'=—CH$_3$ and R=—NH$_2$, i.e. 3,4-dimethoxydianiline (see Example 2 below).

The person skilled in the art has already understood the great interest of the difunctional biphenyl compounds of the invention, particularly as hardeners of monomers or prepolymers to be polymerized (crosslinked) (via adequate functions, capable of reacting with the reactive R groups of said compounds of the invention). Furthermore, the presence of the two aromatic rings in the formula of said compounds has proved to be of particular interest with reference to the mechanical properties and the temperature resistance of the thermosetting products, monomers or prepolymers, which are thermoset (using said hardeners), and the presence of the carbon-carbon bond between said two aromatic rings has proved to be surprisingly opportune with reference to the rate of residual coke after thermal degradation of said products.

It is also necessary to insist on obtaining said difunctional biphenyl compounds of the invention by non-complex implementation processes and, possibly, for many of said compounds, from vanillin, a natural product.

The preparation of the compounds of formula (I) constitutes another object of the invention.

The preparation process in question advantageously comprises:
providing a product selected from vanillin, analogues of vanillin having an —O—(C$_2$-C$_6$)alkyl group in the 3-position, esters of vanillin and analogues of said esters having an —O—(C$_2$-C$_6$)alkyl group in the 3-position;
dimerizing said product to obtain a dimer; and
treating said dimer obtained for the conversion of its phenolic —OH functions to alkoxy functions (—OAlk') and, either of its aldehyde functions to aminomethyl functions (—CH$_2$—NH$_2$), or of its ester functions to isocyanate functions (—N=C=O) or amino functions (—NH$_2$).

The following non-limiting information is provided regarding the reagents and reactions involved.

The provision of the starting products listed above does not pose any particular difficulty to the person skilled in the art. Some of said products are natural products (vanillin; said vanillin and its esters directly obtained from it can therefore be qualified as bio-sourced), some are commercially available, all can be prepared according to synthesis routes familiar to the skilled person (see below).

The process of the invention is advantageously implemented from vanillin. Said vanillin is advantageously of natural origin, extracted from biomass (lignin, in particular wood). Such bio-sourced vanillin is commercially available. It can also be obtained by synthesis, notably from phenol, via guaiacol (phenol chemistry). Synthesis processes of this type are currently being developed on an industrial scale and are, for example, described in *ACS Sustainable Chem. Eng.* 2016, 4, 35-46. Synthetic vanillin is also commercially available.

Vanillin analogues (having an —O—(C$_2$-C$_6$)alkyl group (=—O-alkyl, said linear or branched alkyl group containing from 2 to 6 carbon atoms), advantageously an —Oethyl group, in position 3), can be obtained without particular difficulties, in the same synthesis processes, using, for the etherification of the OH function concerned, instead of dimethyl sulfate ($Me_2SO_4$) or methyl alcohol (MeOH), respectively, di($C_2$-$C_6$)alkyl sulfate or ($C_2$-$C_6$)alkyl alcohol (($C_2$-$C_6$)alkylOH). Ethyl vanillin is also commercially available.

The process of the invention is also advantageously implemented from a vanillin ester (generally a $C_1$-$C_6$ ester, advantageously a $C_1$-$C_4$ ester, very advantageously a $C_1$-$C_2$ ester, preferably the $C_1$ ester (methyl vanillate)). In consideration of the detailed description of the process for preparing the compounds of the following invention, the person skilled in the art will easily conceive the little interest in using an ester whose ester function comprises more than one carbon atom (the ester function being intended to be saponified). Such an ester can easily be prepared from vanillin (if the latter is biosourced, said ester can therefore also be described as biosourced) according to processes described in the prior art, more particularly a two-step process which comprises, successively, an oxidation of the aldehyde function of vanillin to obtain vanillic acid and then an esterification of said acid (in the presence of a suitable alcohol): ($C_1$-$C_6$)alkylOH, advantageously $CH_3OH$ (see above)) in an acid medium. Methyl vanillate is, to date, commercially available.

As regards the analogues of vanillin esters (having an —O—($C_2$-$C_6$)alkyl group (=—O-alkyl, said linear or branched alkyl group containing from 2 to 6 carbon atoms), advantageously an —Oethyl group, in position 3), it is understood that they are obtained by esterification of the corresponding analogues of vanillin (analogues obtained by synthesis from phenol (see above)).

In view of the above, it is understood that the starting product used for the implementation of the process of the invention is:
  advantageously chosen from vanillin and vanillin esters (generally therefore $C_1$-$C_6$ esters, advantageously $C_1$-$C_4$ esters, very advantageously $C_1$-$C_2$ esters, preferably the $C_1$ ester (methyl vanillate)),
  very advantageously selected from vanillin of natural origin (bio-sourced) and esters obtained from vanillin of natural origin (bio-sourced), esters which can therefore be qualified as bio-sourced.

The dimerization of the products made available (starting products) does not pose any difficulties. An oxidative coupling is involved. The use of Laccase derived from *Trametes versicolor* in such a context has been widely described. For example, Examples 1 and 4 of application EP 3 002 333 illustrate the preparation from, respectively, vanillin and methyl vanillate, of divanillin and methyl divanillate (example of divanillin ester).

The dimers obtained have aldehyde or ester functions in positions 1 and 1' and phenolic —OH functions in positions 4 and 4'. It is then necessary to convert, on the one hand, said phenolic —OH functions to —OAlk' alkoxy functions and, on the other hand, said aldehyde or ester functions to the expected reactive group R. The aldehyde functions are converted to aminomethyl functions (—$CH_2$—$NH_2$) and the ester functions to isocyanate functions (—N=C=O) or amino functions (—$NH_2$). It is generally preferable to alkylate (etherify, in a conventional way (see below)) the phenolic —OH functions before converting said aldehyde or ester functions, but it is quite possible to alkylate said phenolic —OH functions during the conversion of said aldehyde or ester functions.

It is a priori not excluded to carry out alkylation after the conversion.

It is proposed hereafter to specify, in no limiting way, the process of the invention, particularly its last step: the step of treatment of the dimer, which therefore includes the two types of conversion mentioned above.

According to a first variant, the product made available is selected from vanillin and vanillin analogues having an —O—($C_2$-$C_6$)alkyl group in the 3-position. The dimerization of said product leads to a dimer selected from divanillin (having an —O—$CH_3$ group in positions 3 and 3') and analogues of divanillin (having an —O—($C_2$-$C_6$)alkyl group in positions 3 and 3'). As regards the treatment of said dimer, it comprises:
  successively, the alkylation (etherification) of the phenolic —OH functions of said dimer then the conversion of the aldehyde functions of said alkylated dimer to oxime functions or the conversion of the aldehyde functions of said dimer to oxime functions then the alkylation (etherification) of the phenolic —OH functions of said dimer with oxime functions, in order to obtain an alkylated divanillyl oxime; advantageously the alkylation (etherification) of the phenolic —OH functions of said dimer then the conversion of the aldehyde functions of said alkylated dimer to oxime functions; and
  reducing said alkylated divanillyl oxime (obtained) to obtain an alkylated divanillyl amine having the formula (I) wherein R=—$CH_2$—$NH_2$.

Said treatment of said dimer comprises preparing an alkylated divanillyl oxime and then reducing it.

The alkylated divanillyl oxime is obtained at the end of the two steps indicated: alkylation (etherification) of the phenolic —OH functions+conversion of the aldehyde functions to oxime functions, implemented in any order, preferably in the order indicated as advantageous. Alkylation (as has been seen, it is more exactly etherification: —OH becomes —OAlk') does not raise any particular difficulties. The dimer with aldehyde functions or the dimer with oxime functions (if the conversion was carried out before alkylation) is generally brought into contact with a base, such as potassium carbonate, in a solvent (such as dimethylformamide (DMF)) and an iodoalkyl (I-Alk', such as iodomethane) is added slowly. The reaction, at high temperature (e.g. 80° C.), takes several hours. At the end of the reaction, the reaction medium is advantageously filtered and the alkylated compound (via the Alk' group) is recovered by precipitation in cold water. The conversion of the aldehyde functions of the dimer or alkylated dimer (if alkylation was carried out before the conversion), in the same way, does not raise any particular difficulties. It is generally carried out in a slightly basic medium (in the presence of sodium acetate, for example), in a solvent (for example ethanol), in the presence of hydroxylammonium chloride. It is carried out at high temperature (for example 100° C.), usually for at least one hour. After extraction of the organic phase, the divanillyl oxime, alkylated or not, contained in it, is recovered by evaporation.

The reduction of the resulting alkylated divanillyl oxime is usually carried out under hydrogen pressure in the presence of a hydrogenation catalyst, such as Raney nickel or palladium on activated carbon.

At the end of this reduction, a product of the invention is obtained of formula (I) wherein R=—$CH_2$—$NH_2$; the values of Alk and Alk' depending, respectively, on the exact nature of the starting product (vanillin, then Alk=—$CH_3$, analogue of vanillin, then Alk=(C$_2$-C$_6$)alkyl) and of the iodoalkyl (I-Alk') used upstream for alkylation.

According to a second variant, the product made available is selected from an ester (generally C$_1$-C$_6$, preferably C$_1$ (see above)) of vanillin (thus having an —O—CH$_3$ group in the 3-position, possibly obtained from vanillin (advantageously of natural origin) or commercially available) and analogues of such an ester (thus having an —O—(C$_2$-C$_6$)alkyl function in the 3-position). The dimerization of said product leads to a dimer selected from the corresponding divanillate (having an —O—CH$_3$ group in position 3 and 3') and the analogues of said corresponding divanillate (having an —O—(C$_2$-C$_6$)alkyl group in position 3 and 3'). With respect to the treatment of said dimer, it comprises:

successively, the saponification of said dimer to obtain a divanillyl acid and the alkylation (etherification) of the phenolic —OH functions of said acid or the alkylation (etherification) of the phenolic —OH functions of said dimer to obtain an alkylated divanillyl ester and the saponification of said alkylated divanillyl ester, to obtain an alkylated divanillic acid; advantageously the saponification of said dimer and the alkylation (etherification) of the —OH functions of the divanillic acid obtained;

acylation of said alkylated divanillic acid to obtain an alkylated acyl diazide; and carrying out a Curtius rearrangement on said alkylated acyl diazide to obtain a dialkoxydiphenylisocyanate having the formula (I) wherein R=—N=C=O; and optionally, in addition, hydrolysis of said dialkoxydiphenyl isocyanate to obtain an alkylated dianiline of formula (I) wherein R=—NH$_2$.

Said treatment of said dimer comprises preparing an alkylated divanillic acid, acylating it, converting it into a dialkoxydiphenylisocyanate of formula (I) wherein R=—N=C=O and optionally converting said dialkoxydiphenylisocyanate of formula (I) wherein R=—N=C=O into an alkylated dianiline of formula (I) wherein R=—NH$_2$.

The alkylated divanillic acid is obtained at the end of the two steps indicated: saponification of the ester functions+ alkylation (etherification) of the phenolic —OH functions, implemented in any order, preferably in the order indicated as advantageous. Saponification is a conventional reaction (it is for example illustrated in Example 13 of application EP 3 002 333). The dimer with its ester functions, optionally alkylated (if alkylation or etherification was carried out before saponification) is usually heated in an alcoholic medium (methanol or ethanol, for example) in the presence of a strong base, such as soda or potash. The reaction, at high temperature (usually at reflux) lasts several hours. Alkylation or etherification is as described above in the context of the first variant.

The acylation of the resulting alkylated divanillic acid is also carried out conventionally. This acid, in a solvent (THF+water mixtures have proved to be very good solvents), is generally first brought into contact with a base (such as triethylamine) and an acyl chloride (such as ethyl chloroformate). Then an acyl azide, preferably sodium azide, is added. Said acylation reaction is carried out in the cold (below room temperature (for example 0° C.)) to avoid any risk of runaway acylation and to minimize the production of by-products.

The alkylated acyl diazide obtained must then be converted to a diisocyanate via a Curtius rearrangement. For this purpose, it is usually dissolved in a dry solvent (for example distilled toluene) under an inert atmosphere (for example nitrogen) and heated. It is heated, advantageously in a Schlenk tube, at a high temperature, for example 80° C., for several hours. At the end of this Curtius rearrangement, a compound of the invention is obtained, of formula (I) wherein R=—N=C=O; the values of Alk and Alk' depending, respectively, on the exact nature of the starting product (a vanillin ester, then Alk=—CH$_3$, an ester of a vanillin analogue, then Alk=—(C$_2$-C$_6$)alkyl) and on that of the iodoalkyl (I-Alk') used upstream for alkylation.

To obtain a compound of formula (I) wherein R=—NH$_2$, the diisocyanate obtained in the previous step is hydrolyzed (in the presence of water). According to a variant, the diisocyanate, in solution in a solvent (for example, toluene), is heated in the presence of a base (such as KOH) in aqueous solution. It is usually heated at high temperature for several hours. It is understood that said compound of formula (I) wherein R=—NH$_2$ is obtained, with the values of Alk and Alk' fixed, respectively, by the exact nature of the starting product and that of the iodoalkyl used upstream for the alkylation (see above).

In view of the above description of the process of the invention, more precisely of its two implementation variants, and of examples 1 and 2 below, it is conceivable that reactions of a type known per se have been arranged within novel reaction schemes to lead to the compounds of the invention.

The reaction schemes for obtaining from vanillin (advantageously of natural origin) the compounds of formula (I) wherein Alk=—CH$_3$ and Alk'=—CH$_3$ are proposed below.

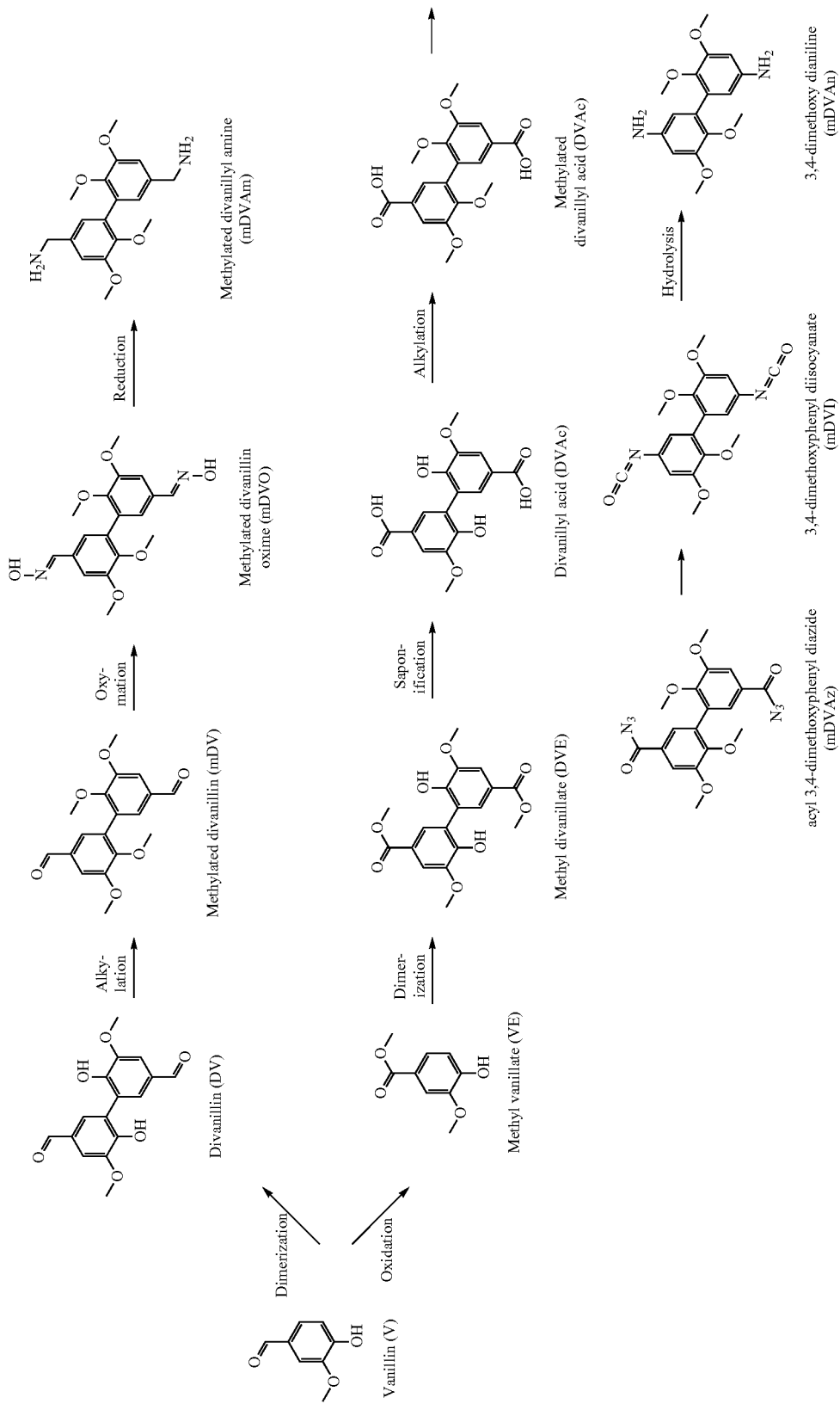

According to another of its objects, the present invention concerns intermediate products, useful for the preparation of the compounds of formula (I), intermediate products with oxime functions (—CH=N—OH functions, precursor of R=CH$_2$NH$_2$) and intermediate products with azide functions (—C(O)—N$_3$ functions, precursor of R=isocyanate (itself precursor of R=—NH$_2$)). It concerns, in fact:

3,4-di(C$_1$-C$_6$)alkoxydivanillyl oximes (see above), with the exception of 3,4-dimethoxydivanillyl oxime (see above example 1c, see FIGS. 1A and 1B), and acyl 3,4-di(C$_1$-C$_6$)alkoxydiphenylazides (see above), especially acyl 3,4-dimethoxydiphenylazide (see above, see Example 2d, see FIGS. 3A and 3B).

According to another of its objects, the present invention also concerns the uses of said compounds of formula (I), described above and/or prepared according to the process described above. It concerns in particular their use as a hardener (crosslinking polymerizing agent or difunctional crosslinking agent) of a thermosetting resin (based on thermosetting monomers or prepolymers (see the introduction of the present text)). Said thermosetting resin can be selected in particular from:

epoxy resins, polycarbonate resins and polycarboxylic acid resins for obtaining, respectively, polyepoxides, poly(hydroxy)urethanes and polyamides (thermoset thermosetting resins). It is obviously understood that the hardeners of the invention which are suitable for reacting with the epoxy, carbonate and carboxylic acid functions are those of formula (I) whose R group contains or consists of an amine function (R=—CH$_2$—NH$_2$ and R=—NH$_2$);

polyol resins and polyamine resins, for obtaining, respectively, polyurethanes and polyamides. It is understood, of course, that the hardeners of the invention which are suitable for reacting with the hydroxyl and amine functions are those of formula (I) wherein the R group is isocyanate.

According to its last object, the invention concerns said thermosetting resins thermoset using a compound of formula (I), as described above and/or prepared according to the process described above, as hardener. It concerns the thermoset resins, obtained by heat treatment, in the presence of at least one hardener chosen from the compounds of formula (I), as described above and/or prepared according to the process described above, of a thermosetting resin, in particular chosen from epoxy resins, polycarbonate resins, polycarboxylic acid resins, (said thermoset resin then being of the polyepoxide, poly(hydroxy)urethane or polyamide type, respectively), polyol resins and polyamine resins (said thermoset resin then being of the polyol or polyamide type, respectively).

It is of course understood that the precursor thermosetting resin has been thermoset using the appropriate hardener of the invention (see above). It is understood that the skeleton of said thermoset resin comprises units corresponding to the "precursor" thermosetting resin (whose reactive functions (epoxy, carbonate, carboxylic acid, alcohol, amine, etc.) have reacted with the reactive functions R of the hardener) and units corresponding to the hardener (whose reactive functions R have reacted with the reactive functions of the "precursor" thermosetting resin (epoxy, carbonate, carboxylic acid, alcohol, amine . . . ).

Among these thermoset (thermosetting) resins, particularly preferred are those of the polyepoxide type, obtained by heat treatment of a thermosetting epoxy resin (for example of the DGEBA type) using a compound of formula (I) wherein R=—CH$_2$—NH$_2$ or —NH$_2$ (advantageously a compound of formula (I) wherein R=—NH$_2$, very advantageously 3,4-dimethoxydianiline), as described above and/or prepared according to the process described above, as hardener. Particularly preferred are those of the polyepoxide type obtained by heat treatment of a thermosetting epoxy resin containing at least one polyepoxide biphenyl compound selected from:

diglycidyl ether of bisphenol, monomer (DGEBA) or oligomer, diglycidyl ether of divanillyl alcohol (DiGEDVA), triglycidyl ether of divanillyl alcohol (TriGEDVA), tetraglycidyl ether of divanillyl alcohol (TetraGEDVA), and mixtures of at least two of said glycidyl ethers of divanillyl alcohol.

It has been seen that the monomer or prepolymer of the DGEBA type has been widely used to date.

The Applicant described di-, tri- and tetraglycidyl ethers of divanillyl alcohol (and their mixtures) as well as other multi-epoxy biphenyl compounds in the as yet unpublished patent application FR 17 60451. All of the multi-epoxy biphenyl compounds described, especially said di-, tri- and tetraglycidyl ethers of divanillyl alcohol (in a mixture or alone), are interesting thermosetting epoxy resin monomers or prepolymers. As regards said di-, tri- and tetraglycidyl ethers of divanillyl alcohol (and their mixtures), they are of particularly interest, hence their association with the hardeners of the invention is currently strongly recommended. The chemical formulae of said glycidyl ethers are shown in the reaction scheme below and in the example section below; the $^1$H and $^{13}$C NMR spectra of said glycidyl ethers are given in said examples and shown in FIGS. 7A-7B, 8A-8B and 9A-9B. A process for their preparation, the reaction scheme of which is given below:

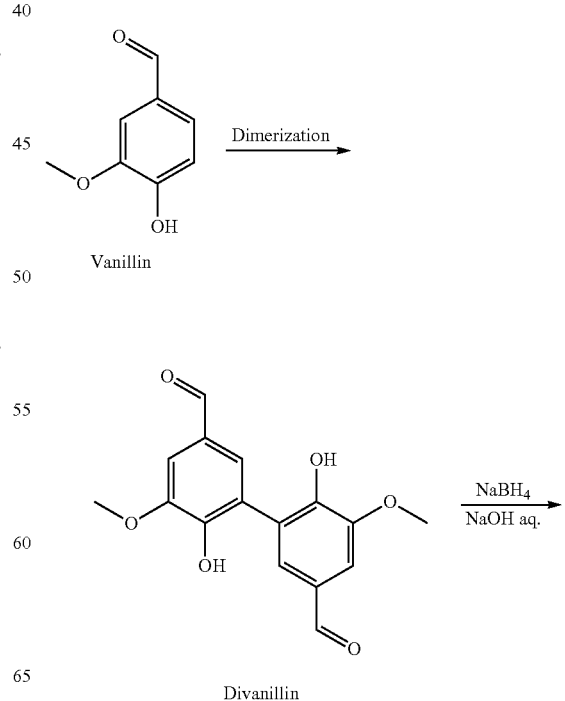

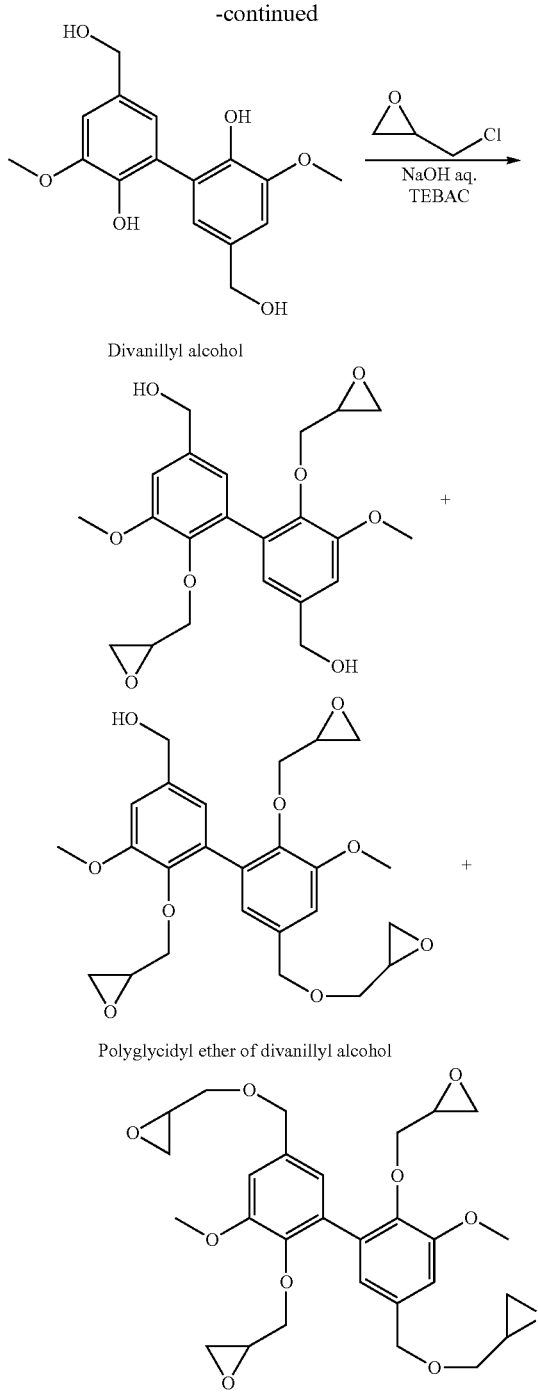

Divanillyl alcohol

Polyglycidyl ether of divanillyl alcohol is precisely described in said example section below (Example 3).

It is easily conceivable that by reacting, instead of epidchlorohydrin (of the formula Cl—CH$_2$-epoxy), an analogue thereof (of the formula Cl—[CH$_2$]$_n$-epoxy, n being an integer from 0 to 6), other ethers of divanillyl alcohol are obtained, which are capable of constituting multi-epoxy biphenyl compounds which can also be thermoset (crosslinked) with the hardeners of the invention.

Incidentally, it can also be noted that the alcohol —CH$_2$OH and hydroxy —OH functions of divanillyl alcohol can also be etherified in two steps (allylation+epoxidation).

In consideration of the above, it is understood that polyepoxides can thus be obtained with bio-sourced epoxy resins and bio-sourced hardeners, the resins and (bio-sourced) hardeners being obtained from vanillin.

The invention is now illustrated by the following examples and the appended figures.

FIGS. 7A to 9A are $^1$H NMR spectra of said isolated multi-epoxide compounds;

FIGS. 7B to 9B are $^{13}$C NMR spectra of said multi-epoxide compounds.

EXAMPLE 1

Figure 1A:
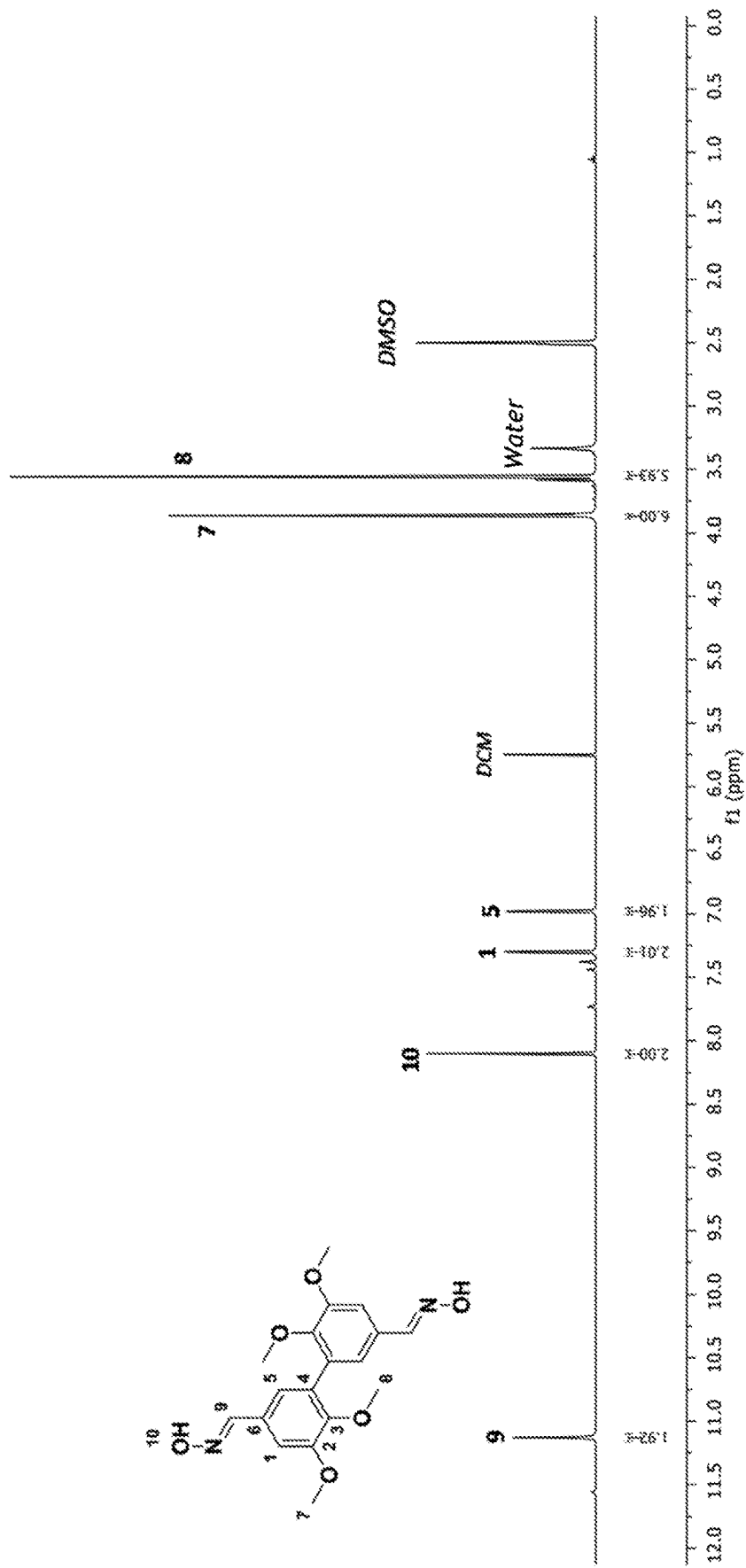
FIGS. 1A and 1B show $^1$H and $^{13}$C NMR spectra of the 3,4-dimethoxydivanillyl oxime (intermediate).

Synthesis of 3,4-dimethoxydivanillylamine (of formula (I) wherein Alk=Alk'=—CH$_3$ and R=—CH$_2$—NH$_2$) from divanillin (DV)

The different steps of the reaction scheme below (corresponding to the one in the first line on page 15) were successively implemented.

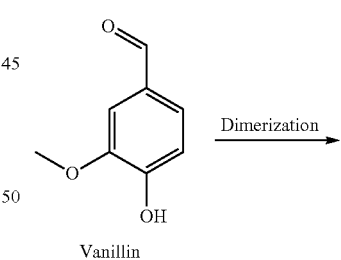

Vanillin

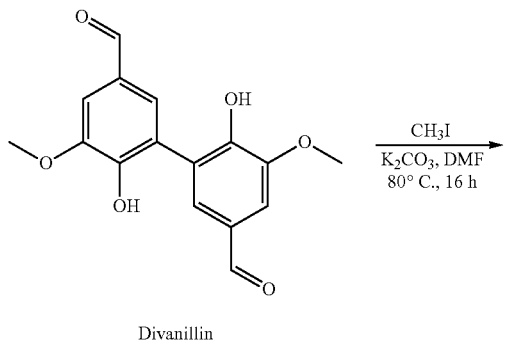

Divanillin

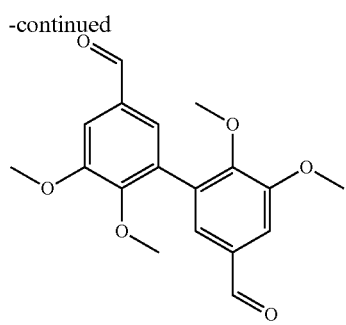

Methyl divanillate

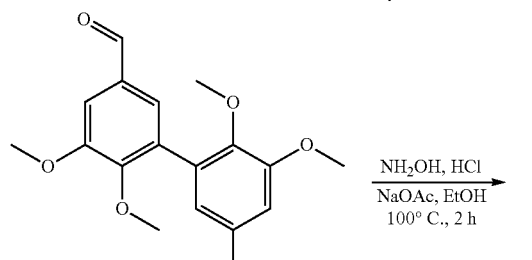

Methyl divanillate

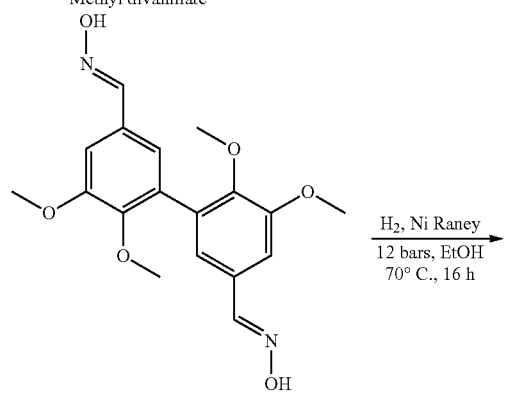

Methyl divanillyl oxime

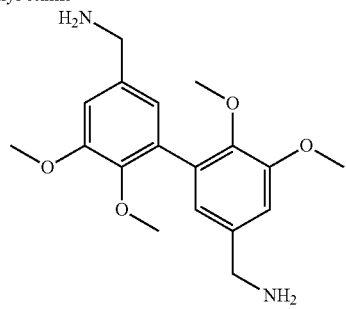

Methyl divanillyl amine

1a. Synthesis of Divanillin (DV)

The preparation of divanillin was carried out according to the procedure described in Example 1 of patent application EP 3 002 333. Specifically, the procedure was as follows.

Vanillin (20 g) (the one used, marketed by the company Acros, was not biosourced. For all intents and purposes, it is indicated that the biosourced vanillin marketed by Borregaard (NO) could have been used) was solubilized in acetone (160 mL) and acetate buffer (1.5 L, prepared from 2.63 g acetic acid and 8.4 g sodium acetate). Laccase from *Trametes versicolor* (170 mg) was added to the resulting mixture. In order to be recycled in active form, said laccase requires oxygen. The reaction medium was therefore left under stirring with constant air bubbling for 24 hours. Divanillin was then recovered by filtration of the buffer solution through a Büchner filter. The filtrate was recovered and reused for further dimerization reactions.

1a'. Purification of Synthesized Divanillin (DV)

Traces of vanillin were likely to be present in the recovered divanillin. To remove them, said divanillin was solubilized in an aqueous solution of NaOH (200 mL at 0.5 M; a few drops of 5 M solution were conveniently added to facilitate solubilization). A large volume of ethanol (600 mL) was then added to the solution as well as an aqueous solution of hydrochloric acid (115 mL at 2 M) until a pH=3 was reached for the mixture. Both divanillin and vanillin are indeed soluble at basic pH in ethanol. Divanillin, on the other hand, is not soluble in ethanol at acidic pH, unlike vanillin. The addition of acid therefore allows the two products to be separated by precipitation of divanillin.

The resulting product was filtered and dried in an oven to remove all traces of solvent.

The synthesis and purification operations were repeated. The yield was approximately 95% each time.

Obtaining divanillin (DV) was confirmed by NMR spectroscopy:

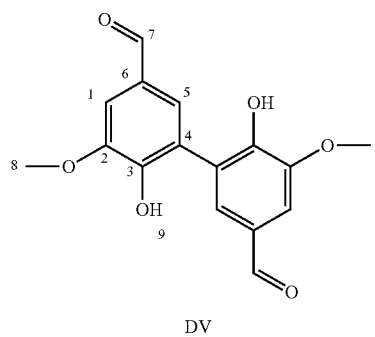

DV $^1$H NMR (400 MHz, DMSO-d6, δ (ppm): δ 9.69 (s, $H_7$), 7.57 (d, $H_1$), 7.16 (d, $H_5$), 3.76 (s, $H_8$).

$^{13}$C NMR (400 MHz, DMSO-d6, δ (ppm)): δ 191.62 (s, $C_7$), 150.88 (s, $C_3$), 148.61 (s, $C_2$), 128.64 (s, $C_6$), 128.21 (s, $C_4$), 125.02 (s, $C_5$), 109.6 (s, $C_1$), 56.25 ($C_8$).

1b. Synthesis of Methylated Divanillin (mDV)

This was done according to the procedure described in Example 9 of patent application EP 3 002 333. Specifically, the procedure was as follows.

26 mmol of divanillin (≈8 g) and 15.2 g of potassium carbonate (110 mmol) were dissolved in 120 mL of DMF. 9.6 mL of iodomethane (158 mmol) was then slowly added to the mixture. After 16 h stirring at 80° C., the mixture was filtered and the resulting solution was poured into cold water. The methylated compound precipitated and was recovered by filtration and dried under vacuum. Yield of 80%.

Obtaining methylated divanillin (mDV) was confirmed by NMR spectroscopy:

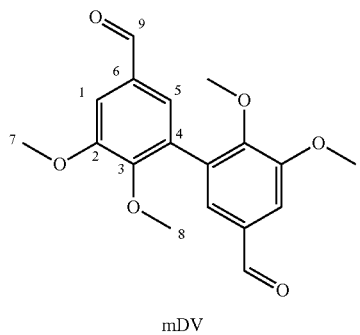
mDV $^1$H NMR (400 MHz, DMSO-d6, δ (ppm)): δ 9.94 (d, H$_9$), 7.58 (d, H$_1$), 7.45 (d, H$_5$), 3.95 (s, H$_7$), 3.67 (s, H$_8$).

$^{13}$C NMR (400 MHz, DMSO-d6, δ (ppm)): δ 152.00 (s, C$_3$), 144.81 (s, C$_2$), 137.64 (s, C$_6$), 132.12 (s, C$_4$), 120.33 (s, C$_5$), 110.18 (s, C$_1$), 62.63 (s, C$_9$), 59.91 (s, C$_8$), 55.52 (C$_7$).

1c. Synthesis of Methylated Divanillyl Oxime (mDVO)

1 g of hydroxylammonium chloride (7 mmol) and 2 g of sodium acetate (12 mmol) were dissolved in 20 mL of ethanol (+4 mL water). 2 g of methylated divanillin (6 mmol) was then added to the mixture. After 2 h at 100° C., the mixture was extracted with dichloromethane (DCM) and washed with water. The organic phase was evaporated using a rotary evaporator. The recovered product was then dried under vacuum. Yield of 85%.

Obtaining methylated divanillin oxime (mDVO) was confirmed by NMR spectroscopy:

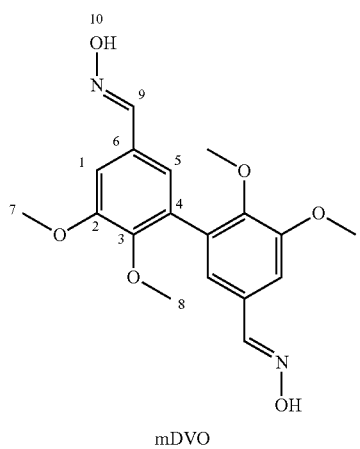
mDVO $^1$H NMR (400 MHz, DMSO-d6, δ (ppm)): δ 11.58 (s, H$_{10}$), 8.10 (s, H$_9$), 7.30 (d, H$_1$), 6.98 (d, H$_5$), 3.87 (s, H$_7$), 3.56 (s, H$_8$).

$^{13}$C NMR (400 MHz, DMSO-d6, δ (ppm)): δ 152.66 (s, C$_2$), 147.81 (s, C$_9$), 147.25 (s, C$_3$), 131.87 (s, C$_6$), 128.69 (s, C$_4$), 121.69 (s, C$_5$), 108.78 (s, C$_1$), 59.88 (s, C$_8$), 55.6 (s, C$_7$).

Figure 1B:
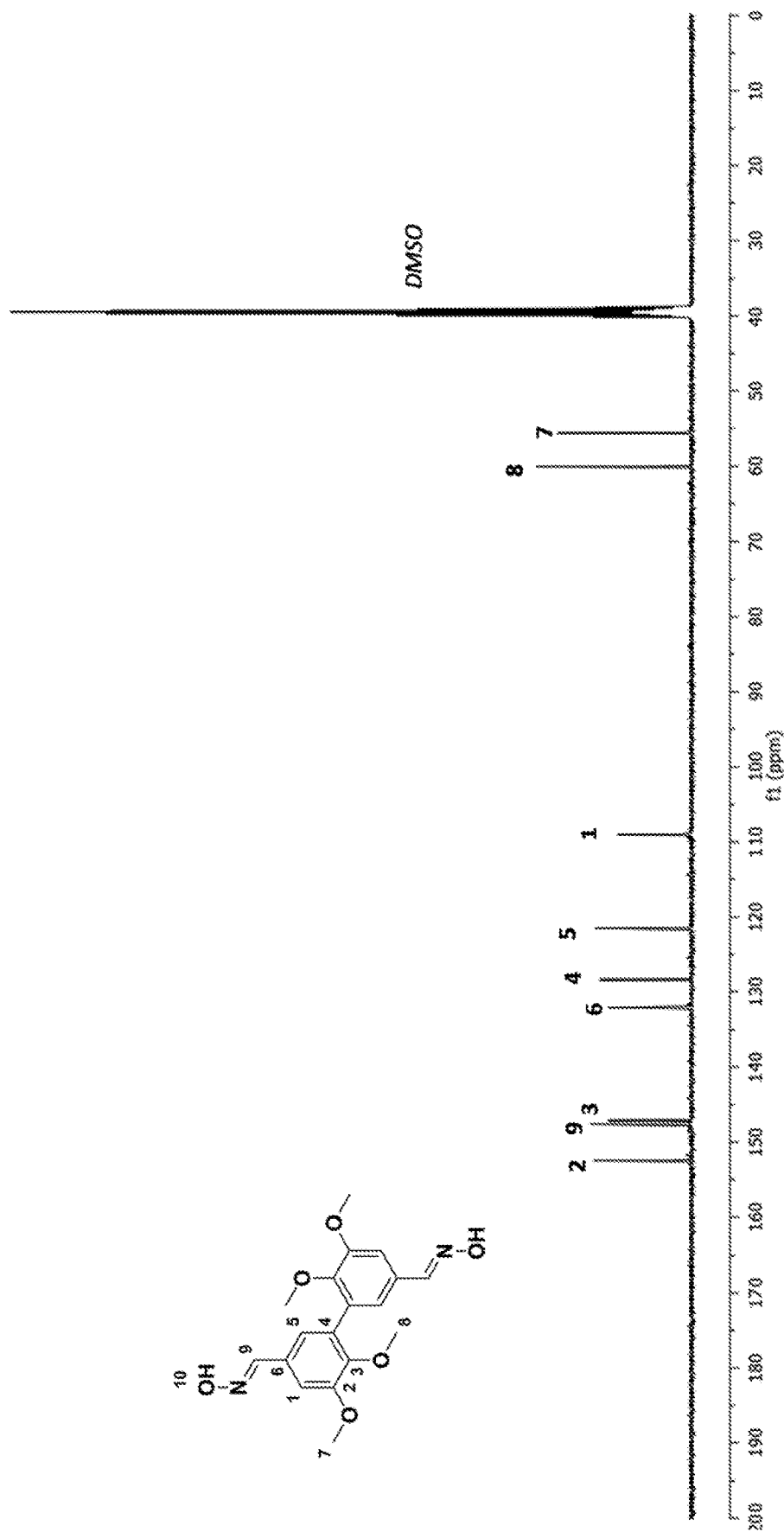

The spectra are shown in FIGS. 1A and 1B respectively.

1d. Synthesis of Methylated Divanillyl Amine (mDVAm)

1 g of methylated divanillyl oxime (2.7 mmol) and 1 mL of Raney nickel were solubilized in 30 mL of ethanol. The mixture was placed in a pressurized reactor under 12 bars of hydrogen. After 16 h at 70° C., the mixture was filtered and the ethanol was evaporated under vacuum. The resulting product was solubilized in dichloromethane (DCM) and washed with water. The DCM was then evaporated under vacuum. Yield of 70%.

Obtaining methylated divanillyl amine (mDVAm) was confirmed by NMR spectroscopy:

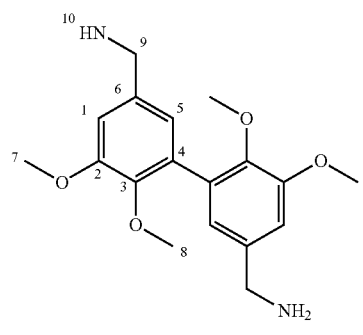
mDVAm $^1$H NMR (400 MHz, DMSO-d6, δ (ppm)): δ 7.04 (m, H$_5$), 6.69 (m, H$_1$), 3.79 (m, H$_8$), 3.63 (s, H$_7$), 3.48 (m, H$_9$).

$^{13}$C NMR (400 MHz, DMSO-d6, δ (ppm)): δ 151.75 (s, C$_2$), 144.46 (s, C$_3$), 136.04 (s, C$_6$), 132.36 (s, C$_4$), 121.78 (s, C$_5$), 111.41 (s, C$_1$), 60.05 (s, C$_8$), 55.65 (s, C$_7$), 51.62 (s, C$_9$).

Figure 2A:
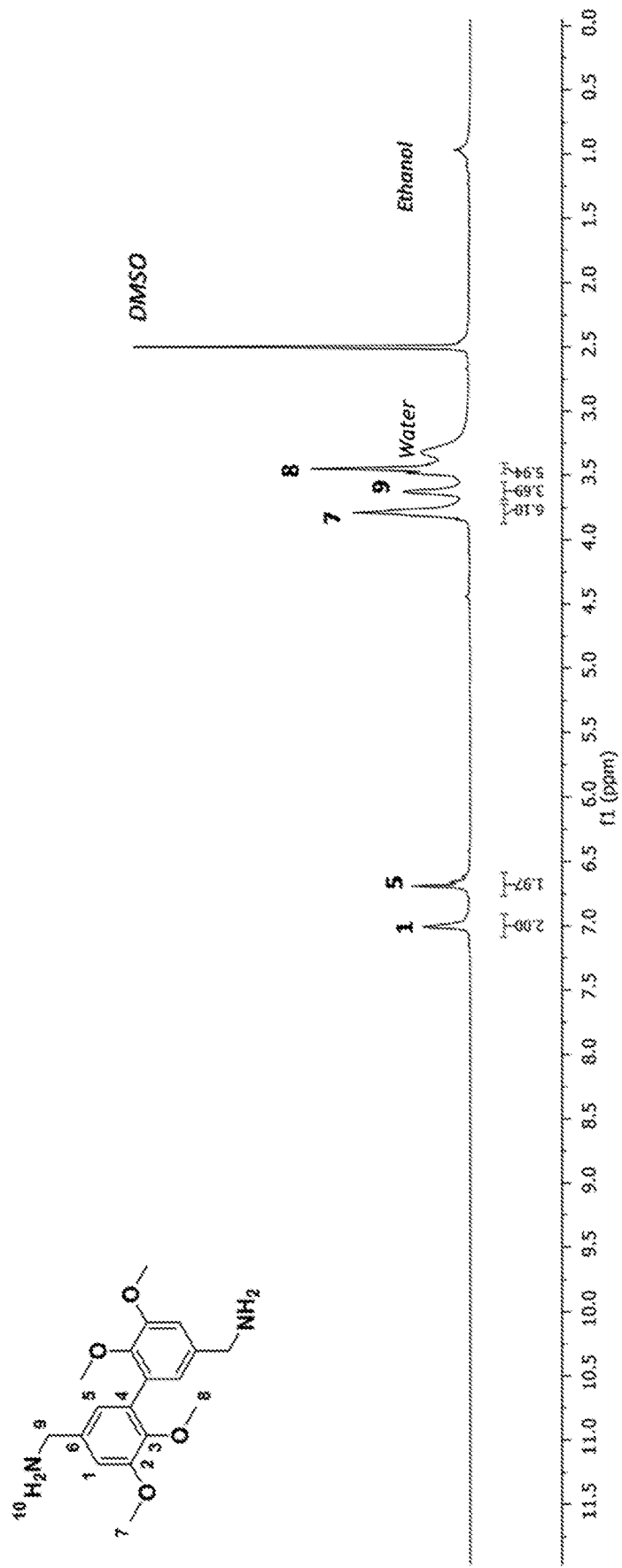
FIGS. 2A and 2B show $^1$H and $^{13}$C NMR spectra of 3,4-dimethoxydivanyllylamine (the compound of the invention (Example 1)).
Figure 2B:
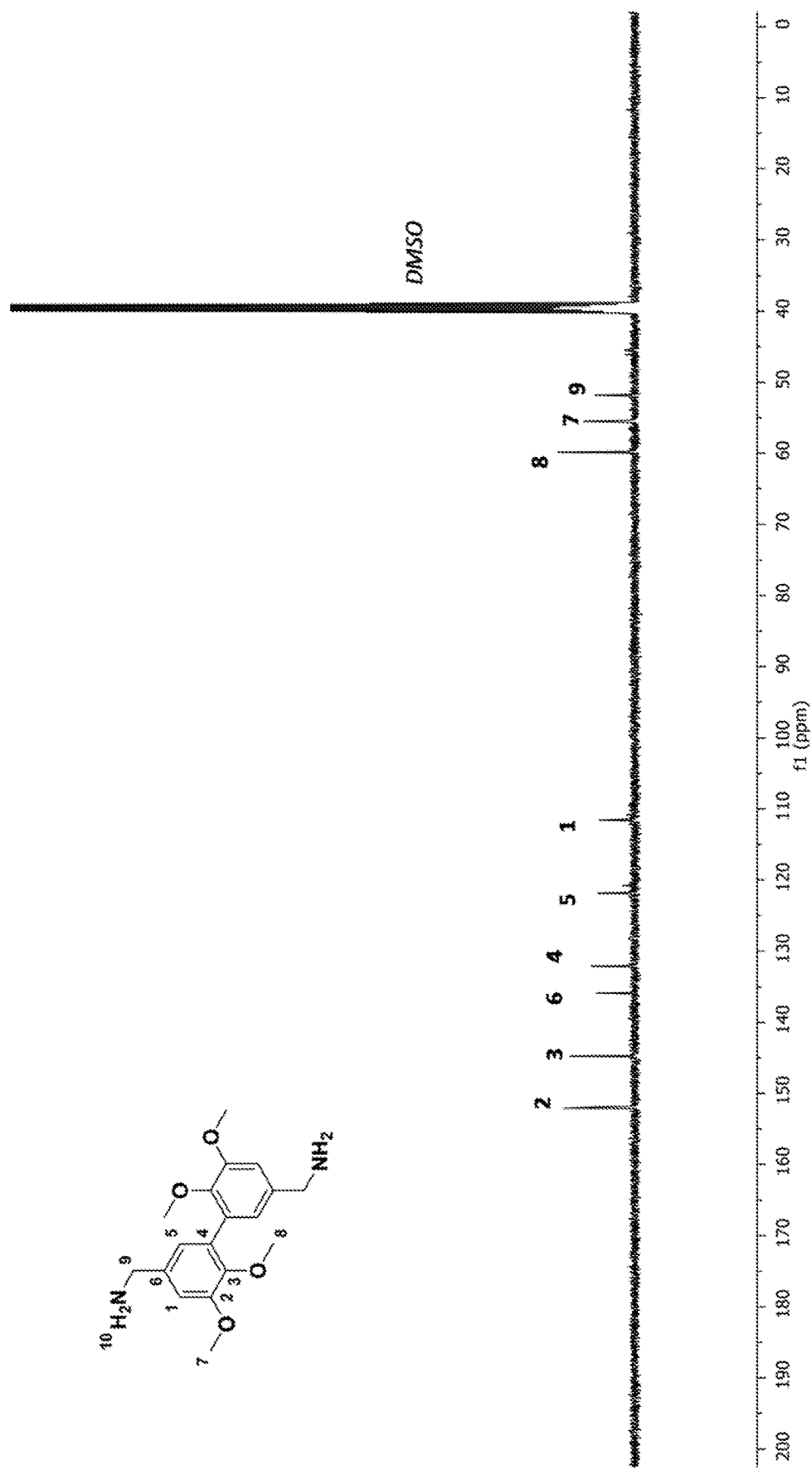

The spectra are shown in FIGS. 2A and 2B respectively.

EXAMPLE 2

Synthesis of 3,4-dimethoxydiphenylisocyanate and 3,4-dimethoxydianiline ((of formula (I) wherein, respectively, Alk=Alk'=—CH$_3$ and R=—N=C=O and Alk=Alk'=—CH$_3$ and R=—NH$_2$) from methyl vanillate The different steps of the reaction scheme below (corresponding to the one in the second line on page 15) were successively implemented.

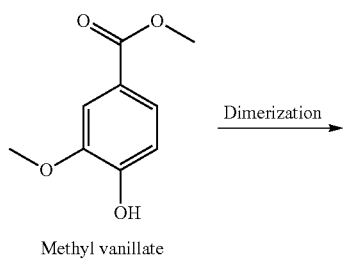
Methyl vanillate

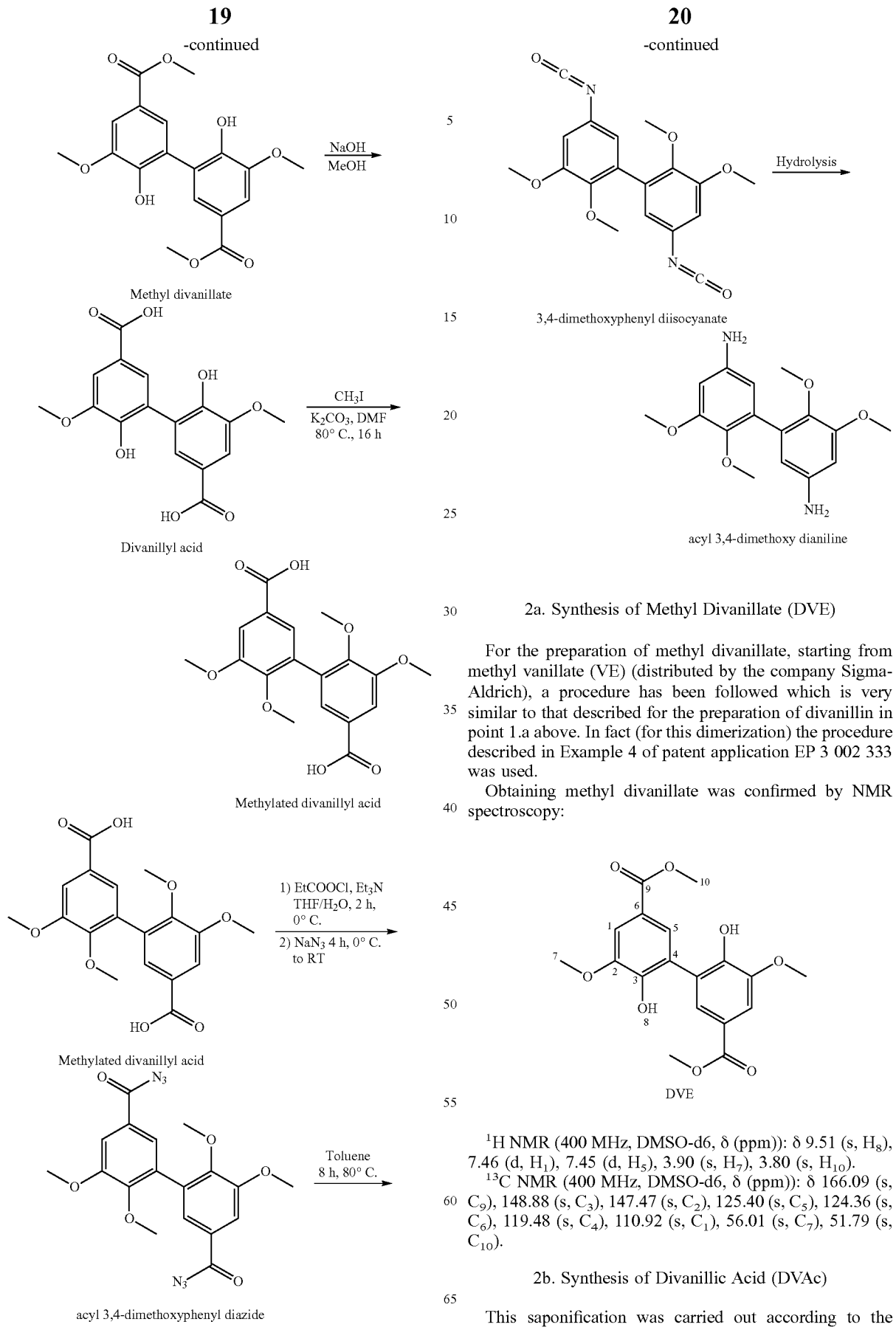

2a. Synthesis of Methyl Divanillate (DVE)

For the preparation of methyl divanillate, starting from methyl vanillate (VE) (distributed by the company Sigma-Aldrich), a procedure has been followed which is very similar to that described for the preparation of divanillin in point 1.a above. In fact (for this dimerization) the procedure described in Example 4 of patent application EP 3 002 333 was used.

Obtaining methyl divanillate was confirmed by NMR spectroscopy:

$^1$H NMR (400 MHz, DMSO-d6, δ (ppm)): δ 9.51 (s, $H_8$), 7.46 (d, $H_1$), 7.45 (d, $H_5$), 3.90 (s, $H_7$), 3.80 (s, $H_{10}$).

$^{13}$C NMR (400 MHz, DMSO-d6, δ (ppm)): δ 166.09 (s, $C_9$), 148.88 (s, $C_3$), 147.47 (s, $C_2$), 125.40 (s, $C_5$), 124.36 (s, $C_6$), 119.48 (s, $C_4$), 110.92 (s, $C_1$), 56.01 (s, $C_7$), 51.79 (s, $C_{10}$).

2b. Synthesis of Divanillic Acid (DVAc)

This saponification was carried out according to the procedure described in Example 13 of patent application EP 3 002 333. Specifically, the procedure was as follows. 10 mmol of methyl divanillate (≈2.5 g) was dissolved in 30 mL of methanol. 3 g of sodium hydroxide solution (75 mmol) were added to the solution. The resulting solution was heated under reflux for 4 h. The reaction was stopped by adding 2.5 mL of water to the reaction medium. The aqueous phase was acidified with hydrochloric acid and the generated diacid precipitated. Yield of 92%.

Obtaining divanillic acid (DVAc) was confirmed by NMR spectroscopy:

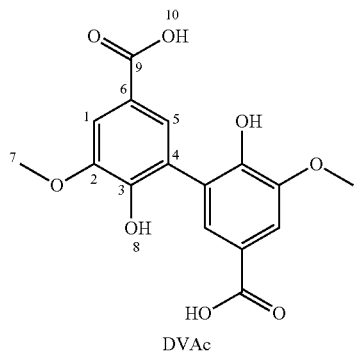

DVAc $^1$H NMR (400 MHz, DMSO-d6, δ (ppm): δ 9.39 (s, H$_8$), 7.45 (d, H$_1$), 7.41 (d, H$_5$), 3.89 (s, H$_7$).

$^{13}$C NMR (400 MHz, DMSO-d6, δ (ppm)): δ 167.18 (s, C$_9$), 148.36 (s, C$_3$), 147.22 (s, C$_2$), 125.44 (s, C$_6$), 124.19 (s, C$_4$), 120.44 (s, C$_5$), 111.05 (s, C$_1$), 55.89 (s, C$_7$).

2c. Synthesis of Methylated Divanillyl Acid (mDVAc)

The etherification was carried out as described above under point 1b, i.e. according to the procedure described in Example 9 of patent application EP 3 002 333. Specifically, the process was as follows.

26 mmol of divanillic acid and 15.2 g of potassium carbonate (110 mmol) were dissolved in 120 mL of DMF. 9.6 mL of iodomethane (158 mmol) was then slowly added to the mixture. After 16 h at 80° C., the mixture was filtered and the resulting solution was poured into cold water. The methylated compound precipitated and was recovered by filtration and dried under vacuum. The typical yield was 80%.

Obtaining methylated divanillic acid (mDVAc) was confirmed by NMR spectroscopy:

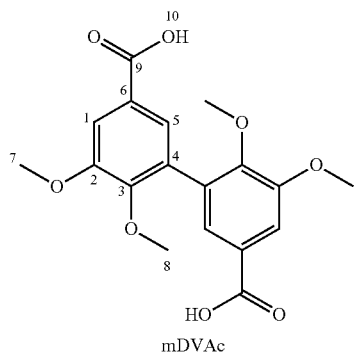

mDVAc $^1$H NMR (400 MHz, DMSO-d6, δ (ppm)): δ 12.94 (s, H$_{10}$), 7.58 (d, H$_1$), 7.39 (d, H$_5$), 3.91 (s, H$_7$), 3.61 (s, H$_8$).

$^{13}$C NMR (400 MHz, DMSO-d6, δ (ppm)): δ 166.83 (s, C$_9$), 152.20 (s, C$_3$), 150.07 (s, C$_2$), 131.34 (s, C$_6$), 125.91 (s, C$_4$), 124.13 (s, C$_5$), 112.93 (s, C$_1$), 60.28 (s, C$_8$), 55.87 (s, C$_7$).

2d. Synthesis of 3,4-Dimethoxydiphenylazide Acyl (mDVAz)

3 mmol of methylated divanillic acid was dissolved in 15 mL of THF and 5 mL of water. The solution was cooled to 0° C. and 2.4 mL of triethylamine in 4 mL of THF were added dropwise to the mixture. 1.8 mL of ethyl chloroformate were then added to the mixture. The resulting mixture was then stirred for 2 h at 0° C. A solution of sodium azide (1.2 g in 4 mL of water) was added dropwise to the mixture and stirred for 2 h at 0° C., then left for 2 h at room temperature. Cold water was then gradually added to the reaction medium to precipitate the solid. The precipitate was filtered and then dissolved in dichloromethane (DCM), washed with water. The organic phase was evaporated using a rotary evaporator. Yield of 60%.

Obtaining 3,4-dimethoxyphenyl acyl diazide (mDVAz) was confirmed by NMR spectroscopy:

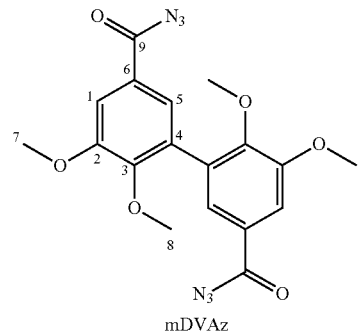

mDVAz $^1$H NMR (400 MHz, CDCl3, δ (ppm)): δ 7.61 (d, H$_1$), 7.55 (d, H$_5$), 3.96 (s, H$_7$), 3.74 (s, H$_8$).

$^{13}$C NMR (400 MHz, CDCl3, δ (ppm)): δ 171.85 (s, C$_9$), 152.79 (s, C$_3$), 152.39 (s, C$_2$), 131.69 (s, C$_6$), 125.81 (s, C$_4$), 125.23 (s, C$_5$), 112.78 (s, C$_1$), 61.10 (s, C$_8$), 56.22 (s, C$_7$).

Figure 3A:
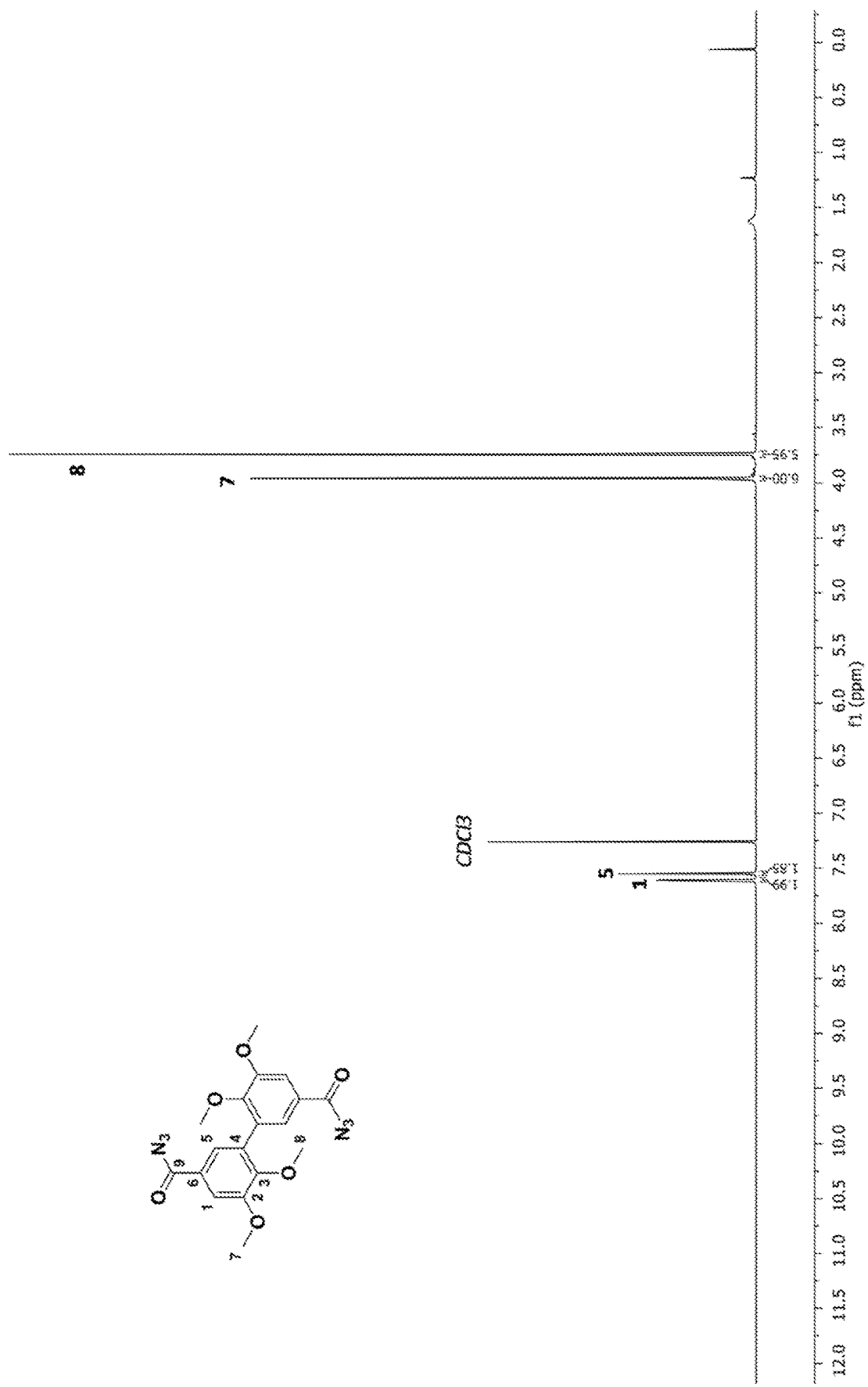
FIGS. 3A and 3B show $^1$H and $^{13}$C NMR spectra of 3,4-dimethoxydiphenylazide acyl (intermediate).
Figure 3A:
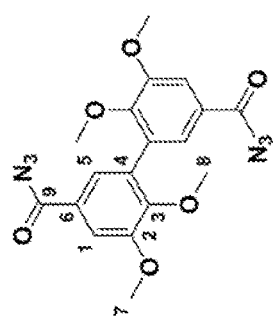
Figure 3B:
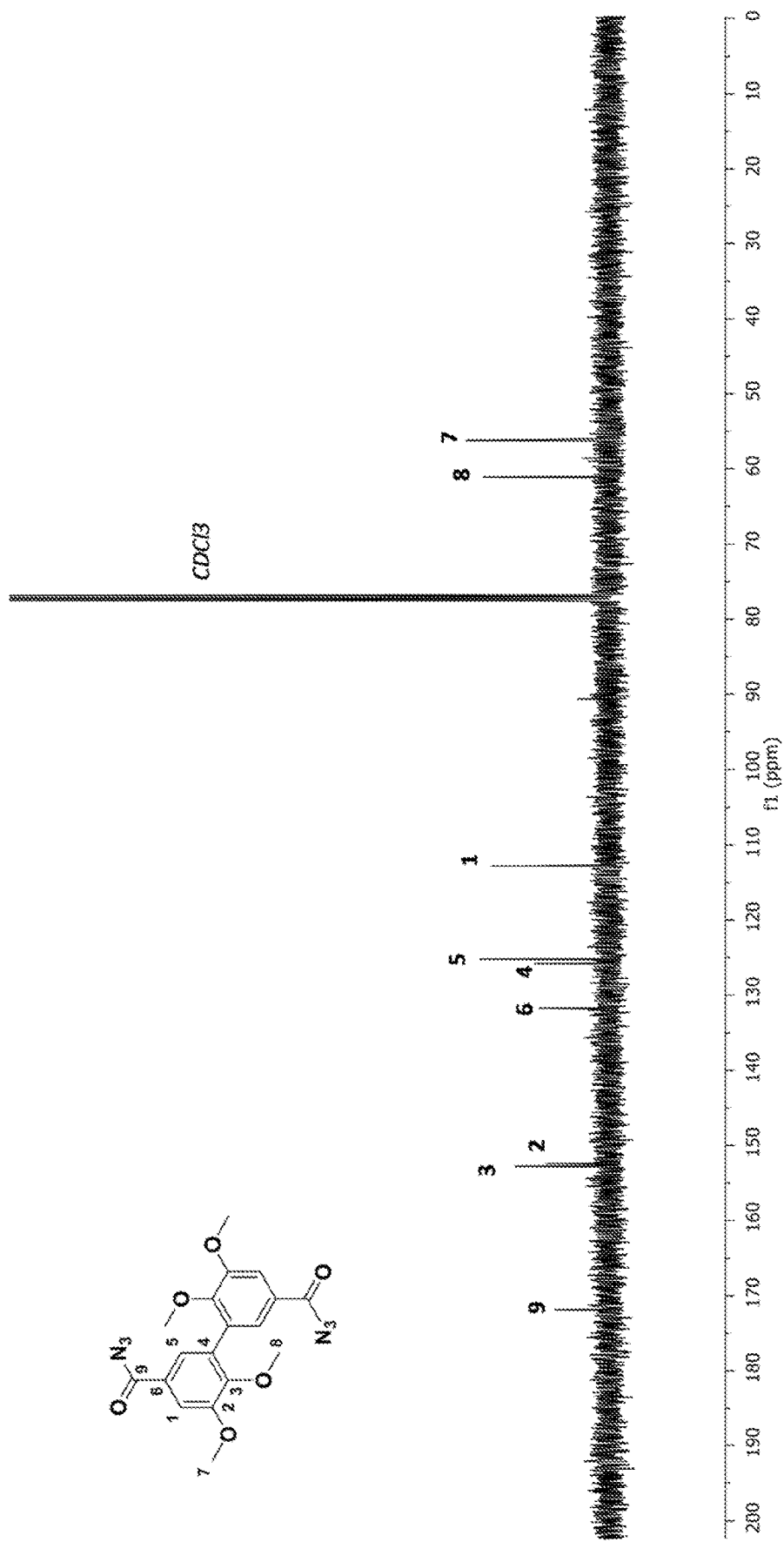

The spectra are shown in FIGS. 3A and 3B respectively.

2e. Synthesis of 3,4-Dimethoxydiphenylisocyanate (mDVI)

In a Schlenk tube under inert atmosphere (nitrogen), 0.5 mmol of 3,4-dimethoxyphenyl acyl diazide was dissolved in 3 mL of dry toluene. The mixture was stirred and heated to 80° C. for 8 h. The toluene was then evaporated using a rotary evaporator at 60° C. Yield of 80%.

Obtaining 3,4-dimethoxyphenyl diisocyanate (mDVI) was confirmed by NMR spectroscopy:

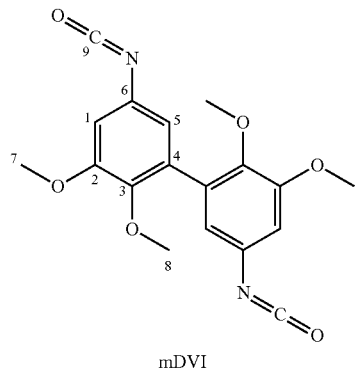

mDVI $^1$H NMR (400 MHz, CDCl3, δ (ppm)): δ 6.65 (d, $H_1$), 6.58 (d, $H_5$), 3.88 (s, $H_7$), 3.64 (s, $H_8$).

$^{13}$C NMR (400 MHz, CDCl3, δ (ppm)): δ 153.41 (s, $C_3$), 144.82 (s, $C_2$), 132.46 (s, $C_6$), 128.72 (s, $C_4$), 124.71 (s, $C_9$), 118.91 (s, $C_5$), 108.86 (s, $C_1$), 60.99 (s, $C_8$), 56.13 (s, $C_7$).

Figure 4A:
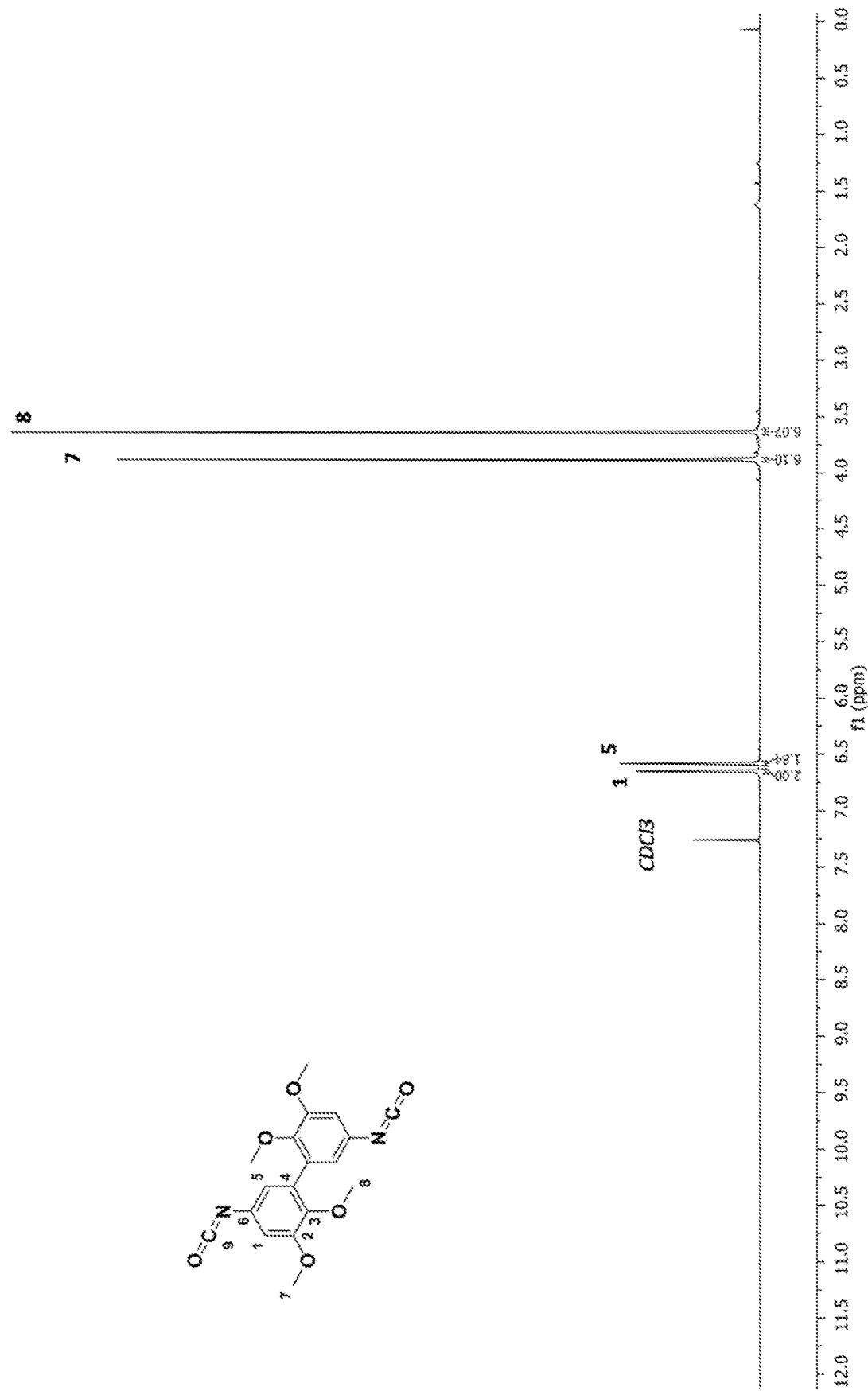
FIGS. 4A and 4B show the $^1$H and $^{13}$C NMR spectra of 3,4-dimethoxydiphenylisocyanate (the compound of the invention (Example 2)).
Figure 4B:
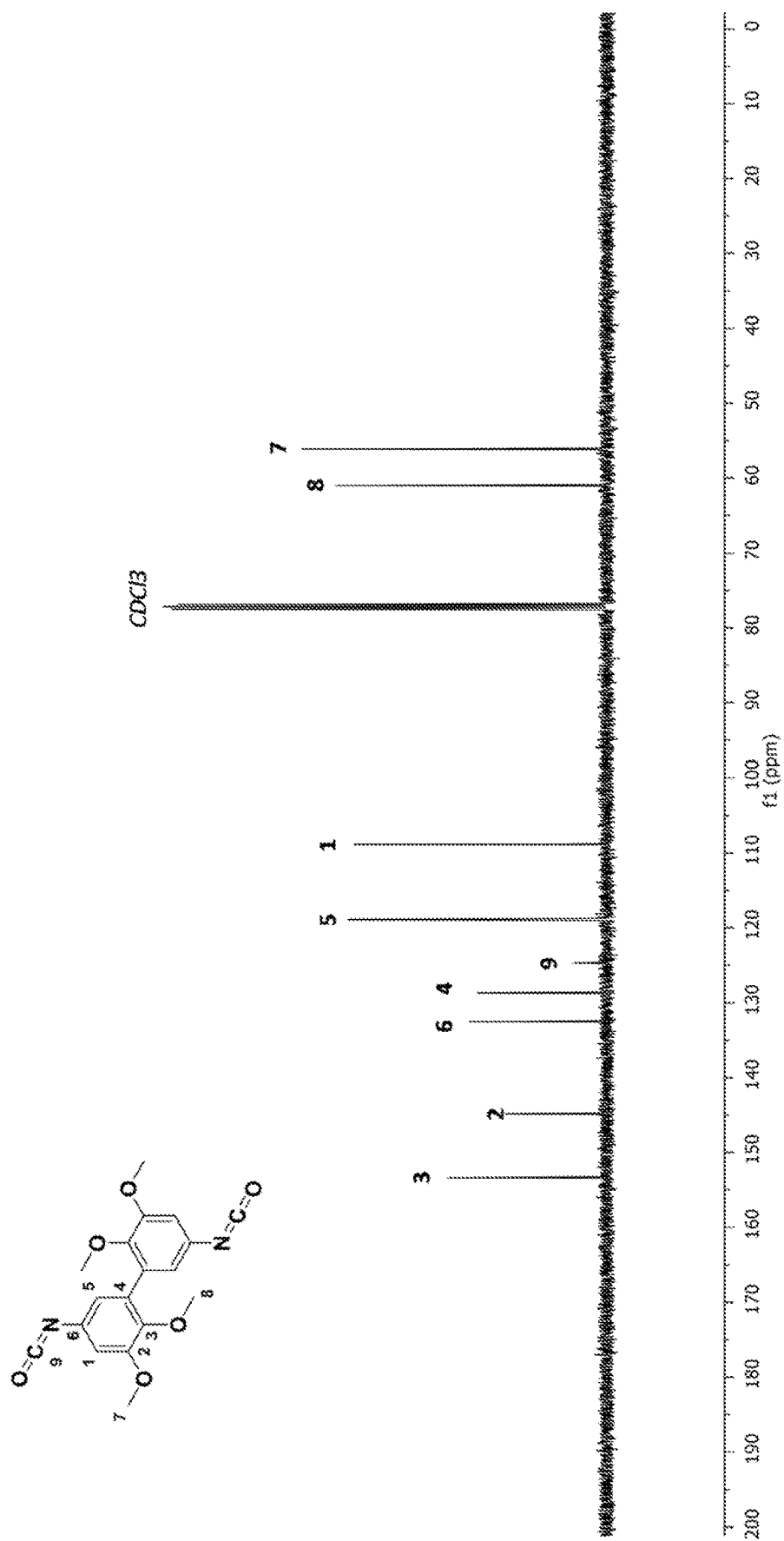

The spectra are shown in FIGS. 4A and 4B respectively.

2f. Synthesis of 3,4-Dimethoxydianiline (mDVAn)

3 mmol of potassium hydroxide were added to 0.75 mmol of 3,4-dimethoxyphenyl diisocyanate in solution in toluene. The mixture was stirred and heated for 12 h at 80° C. The toluene was evaporated under vacuum. The resulting product was solubilized in ethyl acetate and washed with water. The organic phase was then evaporated using a rotary evaporator. Yield of 10%.

Obtaining 3,4-dimethoxyphenyldianiline (mDVAn) was confirmed by NMR spectroscopy:

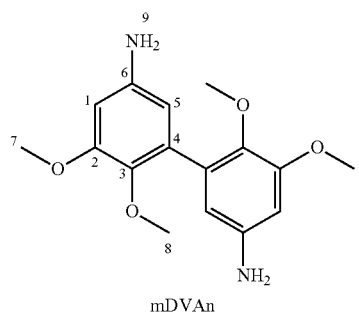

mDVAn $^1$H NMR (400 MHz, CDCl3, δ (ppm)): δ 6.23 (d, $H_1$), 5.90 (d, $H_5$), 4.79 (s, $H_9$), 3.72 (s, $H_7$), 3.38 (s, $H_8$).

$^{13}$C NMR (400 MHz, CDCl3, δ (ppm)): δ 152.47 (s, $C_3$), 144.22 (s, $C_2$), 136.90 (s, $C_6$), 133.35 (s, $C_4$), 107.48 (s, $C_5$), 98.42 (s, $C_1$), 59.97 (s, $C_8$), 55.18 (s, $C_7$).

Figure 5A:
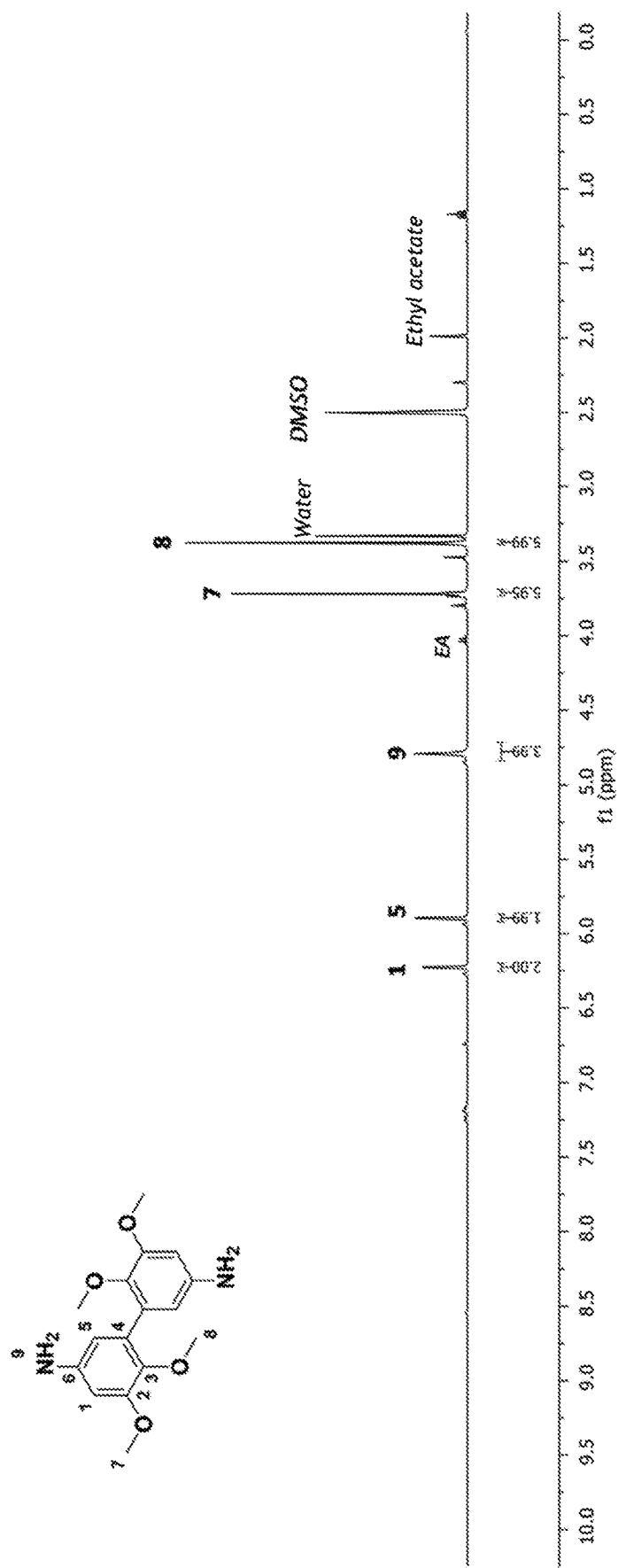
FIGS. 5A and 5B show the $^1$H and $^{13}$C NMR spectra of 3,4-dimethoxydianiline (the compound of the invention (Example 2)).
Figure 5B:
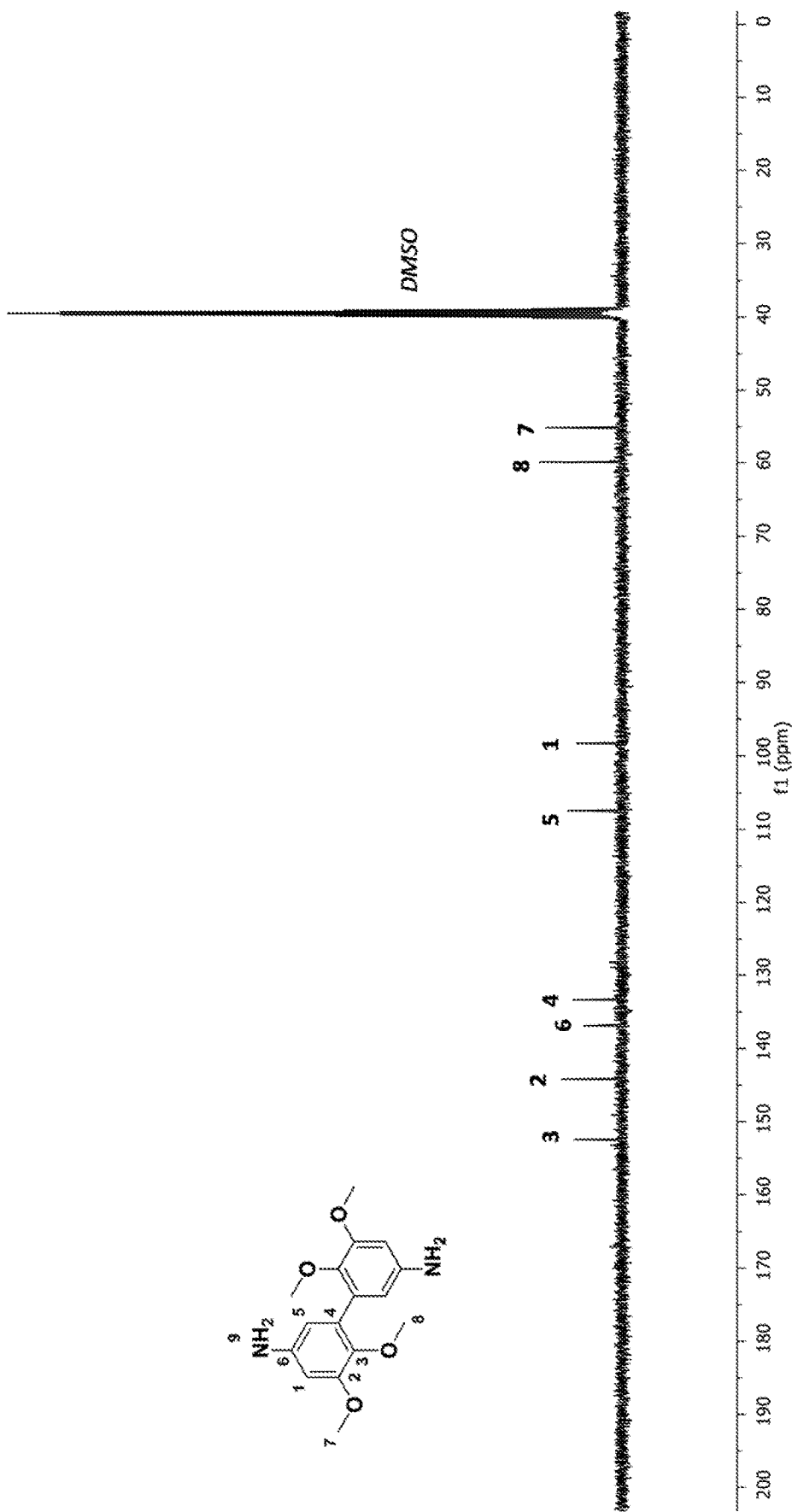

The spectra are shown in FIGS. 5A and 5B respectively.

EXAMPLE 3

Polyepoxides Obtained from a Thermosetting Epoxy Resin and a Hardener

The epoxy resins used were:
diglycidyl ether of bisphenol A (DGEBA), of formula:

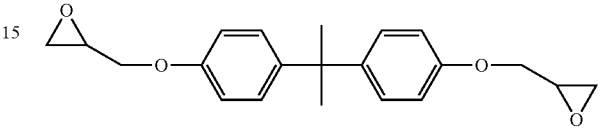

marketed by Sigma-Aldrich under the trade name D.E.R.® 332, and the tetraglycidyl ether of divanillyl alcohol (TetraGEDVA), the preparation and formula of which are specified below.

TetraGEDVA was obtained (like its homologues: di- and tri-epoxidised (DiGEDVA and TriGEDVA) (see below)) under the conditions specified below, from divanillin, synthesized and purified under the conditions described in Example 1 above (more precisely in points 1a and 1a' of said Example 1).

A) From said divanillin, divanillyl alcohol was first prepared as follows (it would have been possible to proceed according to Example 8 of patent application EP 3 002 333).

The purified divanillin (20 g) was reduced with sodium borohydride (NaBH$_4$) to form divanillyl alcohol. To this end, it was solubilized in 0.5 M sodium hydroxide (180 mL; a few drops of 5 M solution were conveniently added to facilitate solubilization). Then NaBH$_4$ (3 g) was added and the resulting mixture was kept under stirring until completely dissolved. After one hour of stirring, the reaction was stopped by adding, dropwise, an aqueous solution of hydrochloric acid (160 mL at 2 M) until a pH=3 was reached. The divanillyl alcohol then precipitated. It was recovered by filtration. The recovered product was dried in an oven. Synthesis was repeated. The yield was approximately 80% each time.

Obtaining divanillyl alcohol (DVA) was confirmed by NMR spectroscopy:

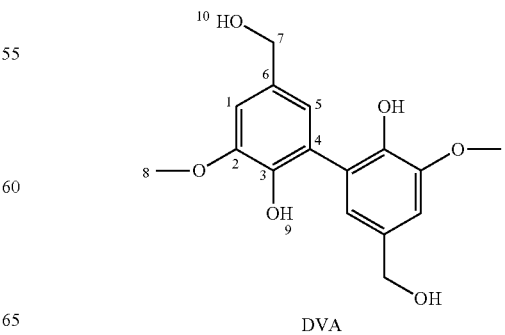

DVA

1H NMR (400 MHz, DMSO-d6, δ (ppm)): δ 8.22 (s, H9), 6.88 (d, H1), 6.67 (d, H5), 5.01 (t, H10), 4.41 (d, H7), 3.82 (s, H8).

$^{13}$C NMR (400 MHz, DMSO-d6, δ (ppm)): δ 147.94 (s, C3), 142.77 (s, C2), 133.08 (s, C6), 125.92 (s, C4), 121.83 (s, C5), 109.50 (s, C1), 63.38 (s, C7), 56.25 (s, C8).

B) The resulting divanillyl alcohol was then epoxidized with epichlorohydrin under "different" conditions to obtain different mixtures of several multi-epoxide compounds.

Figure 6:
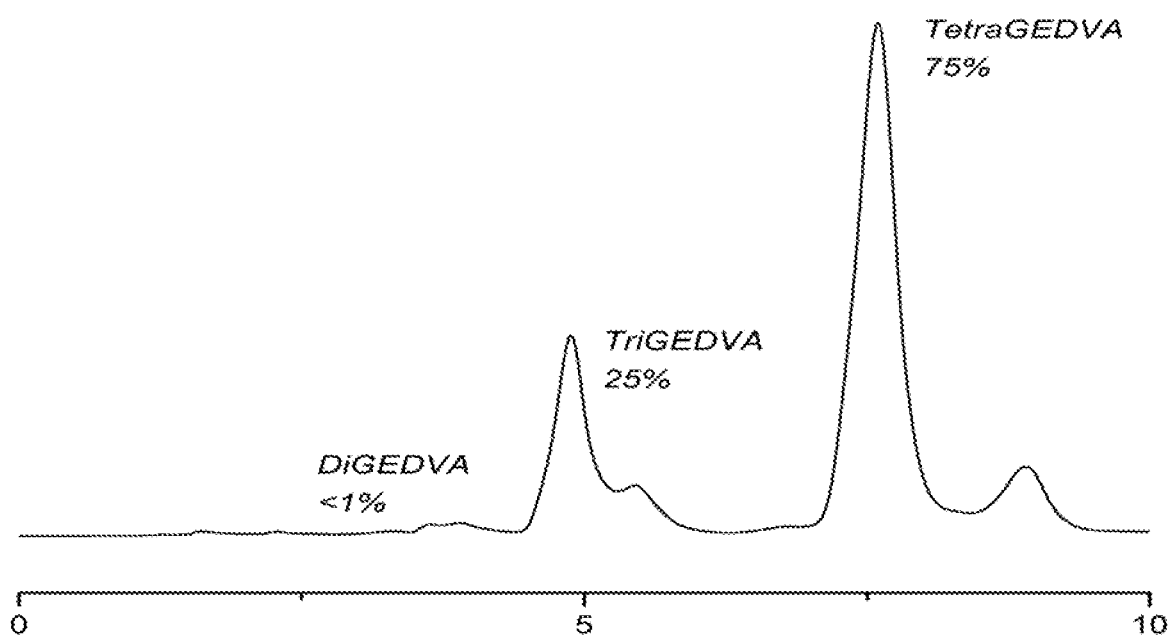
FIG. 6 shows the result of chromatography on a mixture of polyepoxide compounds (polyglycidyl ethers of divanillyl alcohol) (Example 3).

B1) The conditions used to obtain a mixture of 25% TriGEDVA and 75% TetraGEDVA (% by mass) are described in detail below. In a first step, divanillyl alcohol (20 g) was mixed with epichlorohydrin (100 mL) and tetrabutylammonium bromide (TEBAC) (2 g). TEBAC is a phase transfer agent that allows phenol to react with epichlorohydrin, introduced in excess to form a di-epoxide. The reaction mixture was left under stirring at 80° C. for 1.5 h; then it was cooled to room temperature. Subsequently, an aqueous sodium hydroxide (NaOH) solution (160 mL at 10 M: 10 NaOH eq./OH) was added. The addition of the base closed the open epoxides but also deprotonated the benzyl alcohols which, in turn, were epoxidized by nucleophilic substitution with epichlorohydrin. The solution was then mechanically stirred for 20 h in a cold water bath. At the end of the reaction, dichloromethane (DCM) (300 mL) was added to the reaction medium to precipitate the salts (NaCl). The liquid phases were separated from the reaction medium and the salts rinsed off with 100 mL of DCM. The liquid phases were combined and the aqueous phase was extracted with 2×50 mL of DCM. The individual organic phases were combined and washed with 100 mL of water. The organic phase was concentrated using a rotary evaporator and the epichlorohydrin was finally evaporated under vacuum. The yield was quantitative. The proportion of di-, tri- and tetra-epoxide compounds was quantified by high-performance liquid chromatography (HPLC). The apparatus used was a SpectraSYSTEM®, mounted with a Phenomenex 5p C18 100A column. The detector used was a SpectraSYSTEM® UV2000 system from Thermo Separation Products. The analyses were performed with an eluent composed of acetonitrile and water in a 50/50 isocratic proportion. The chromatograph obtained is shown in the attached FIG. 6.

B2) The procedure described in B1) above was reproduced (in all respects) but with the addition of an aqueous solution of NaOH (50 mL at 5 M) and with mechanical stirring for only 1 h. A mixture of 80% DiGEDVA, 15% TriGEDVA and 5% TetraGEDVA (% by mass) was then obtained.

B3) The procedure described in B1) above was repeated (in all respects) but with the addition of an aqueous solution of NaOH (50 mL at 5 M) and with mechanical stirring for only 8 h. A mixture of 35% DiGEDVA, 50% TriGEDVA and 15% TetraGEDVA (% by mass) was then obtained.

In order to obtain, in isolation, the various multi-epoxide compounds (di-, tri- and tetraepoxides, constituent elements of epoxy resins (taken alone or in a mixture)), a purification step by flash or instantaneous chromatography, on a Grace Reveleris® apparatus, equipped with a silica cartridge and a UV detector, was carried out on the mixtures, using a dichloromethane/methanol solvent gradient of 99/1 to 90/10 (by volume) for 30 minutes.

The identity of these multi-epoxide compounds was confirmed by NMR spectroscopy:

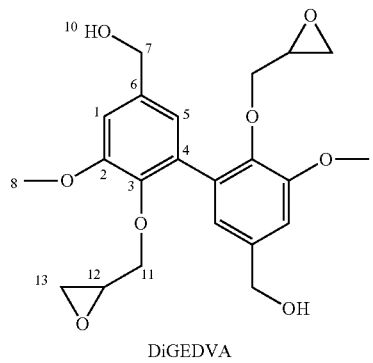

DiGEDVA $^{1}$H NMR (400 MHz, DMSO-d6, δ (ppm)): δ 7.0 (d, H$_1$), 6.71 (d, H$_5$), 5.16 (t, H$_{10}$), 4.47 (d, H$_7$), 3.88 (m, H$_{11}$), 3.83 (s, H$_8$), 3.74 (m, H$_{11b}$), 2.95 (m, H$_{12}$), 2.6 (t, H$_{13}$), 2.36 (t, H$_{13b}$).

$^{13}$C NMR (400 MHz, DMSO-d6, δ (ppm)): δ 152.33 (s, C$_3$), 144.47 (s, C$_2$), 138.26 (s, C$_6$), 132.59 (s, C$_4$), 120.86 (s, C$_5$), 110.79 (s, C$_1$), 74.22 (s, C$_{11}$), 63.14 (s, C$_7$), 56.18 (s, C$_8$), 50.53 (s, C$_{12}$), 43.97 (s, C$_{13}$).

Figure 7A:
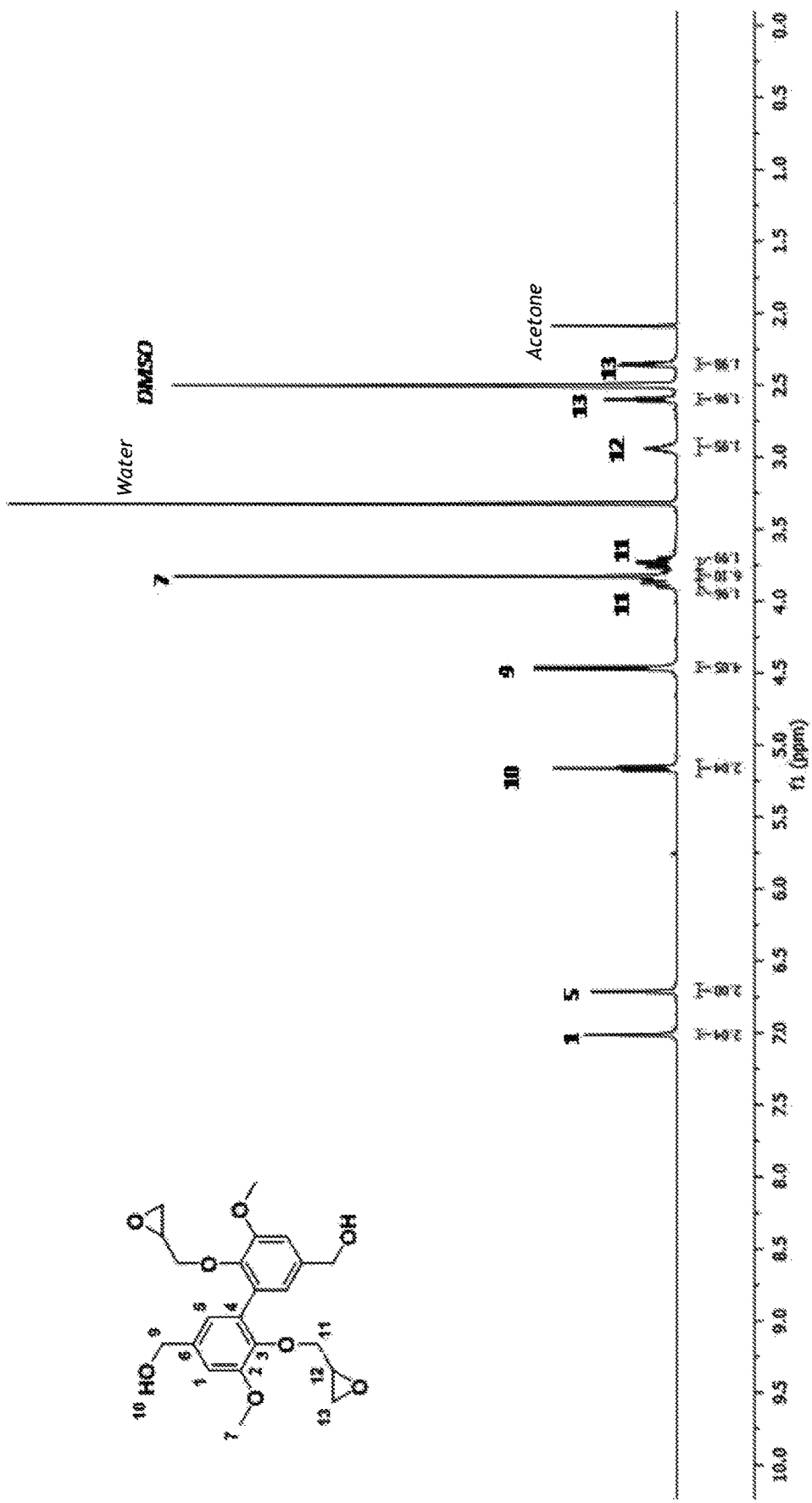
Figure 7B:
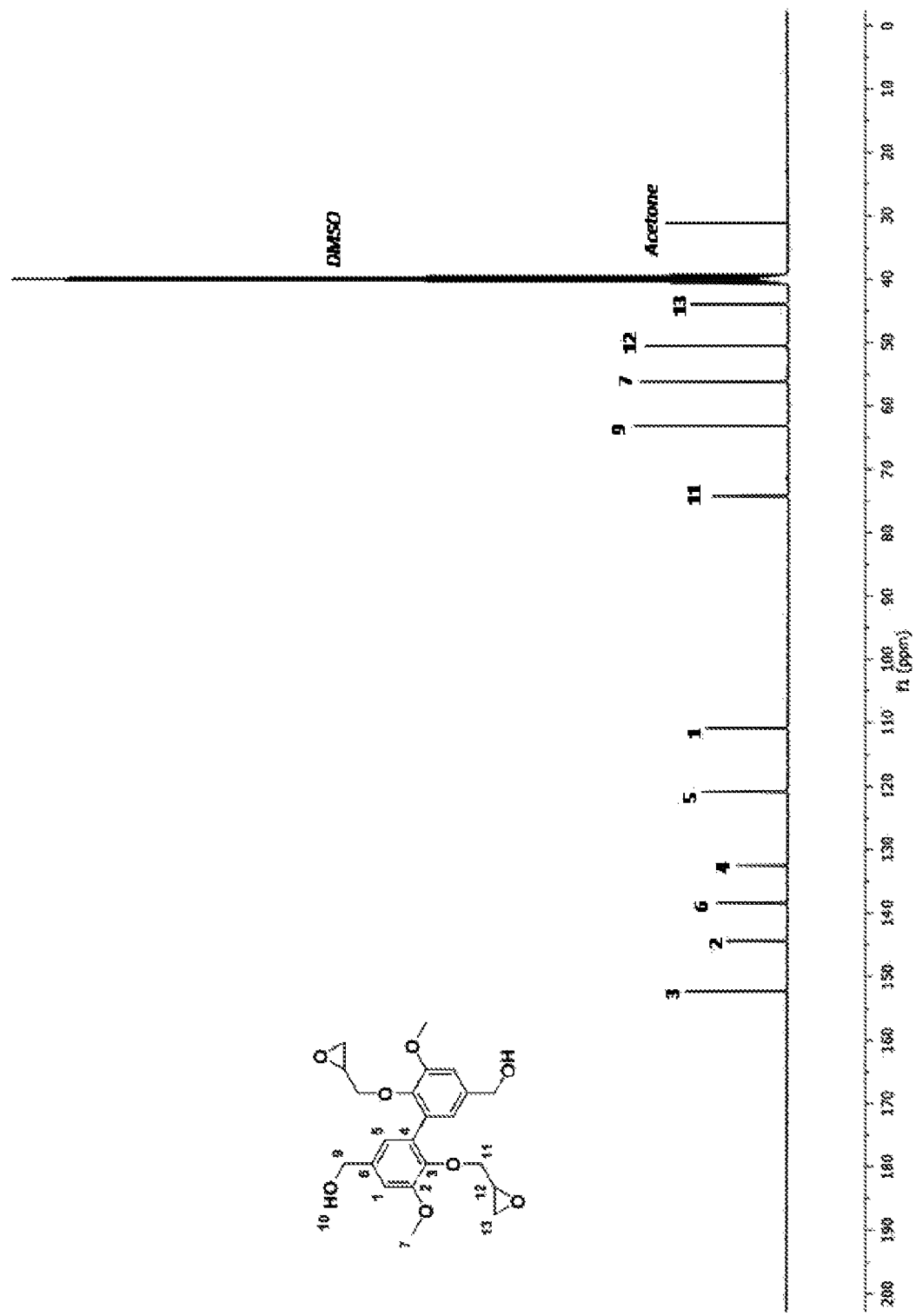

The spectra are shown in FIGS. 7A and 7B respectively.

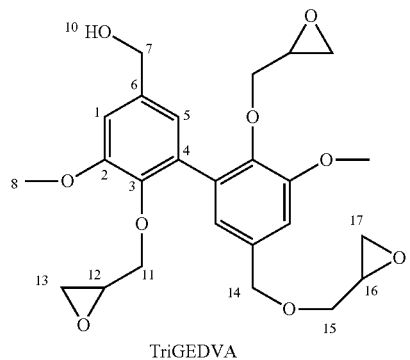 [SMILES: COc1cc(CO)cc(-c2cc(COCC3CO3)cc(OC)c2OCC2CO2)c1OCC1CO1 ; "TriGEDVA"]

TriGEDVA $^{1}$H NMR (400 MHz, DMSO-d6, δ (ppm)): δ 7.01 (d, H$_1$), 6.75 (d, H$_5$), 5.18 (t, H$_{10}$), 4.47 (d, H$_7$ H$_{14}$)$_1$ 3.92 (m, H$_1$), 3.84 (s, H$_8$), 3.76 (m, H$_{11b}$), 3.69 (m, H$_{15}$), 3.29 (m, H$_{15b}$), 3.14 (m, H$_{16}$), 2.97 (m, H$_{12}$), 2.72 (m, H$_{17}$), 2.6 (m, H$_{13}$), 2.5 (m, H$_{17b}$), 2.36 (m, H$_{13b}$). $^{13}$C NMR (400 MHz, DMSO-d6, δ (ppm)): δ 152.02 (s, C$_{3'}$), δ 151.89 (s, C$_3$), 144.38 (s, C$_{2'}$), 143.68 (s, C$_2$), 138.12 (s, C$_6$), 133.39 (s, C$_{6'}$), 132.06 (s, C$_{4'}$), 131.76 (s, C$_4$), 121.78 (s, C$_5$—), 120.26 (s, C$_5$), 111.55 (s, C$_{1'}$), 110.46 (s, C$_1$), 73.85 (s, C$_{14}$), 71.81 (s, C$_{15}$), 70.79 (s, C$_{11}$), 62.67 (s, C$_7$), 55.90 (s, C$_8$), 50.42 (s, C$_{12}$), 50.16 (s, C$_{16}$), 43.42 (s, C$_{13}$ C$_{17}$).

Figure 8A:
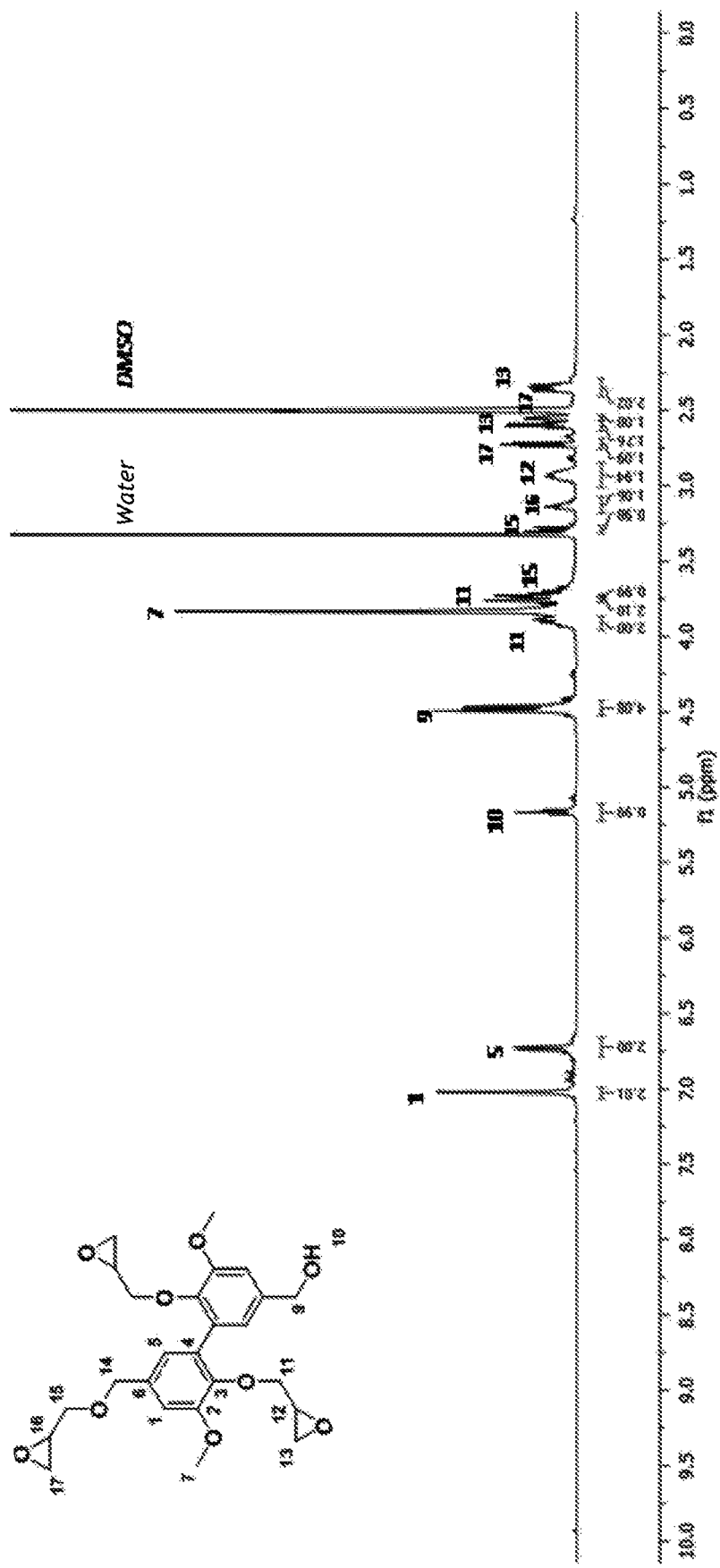
Figure 8B:
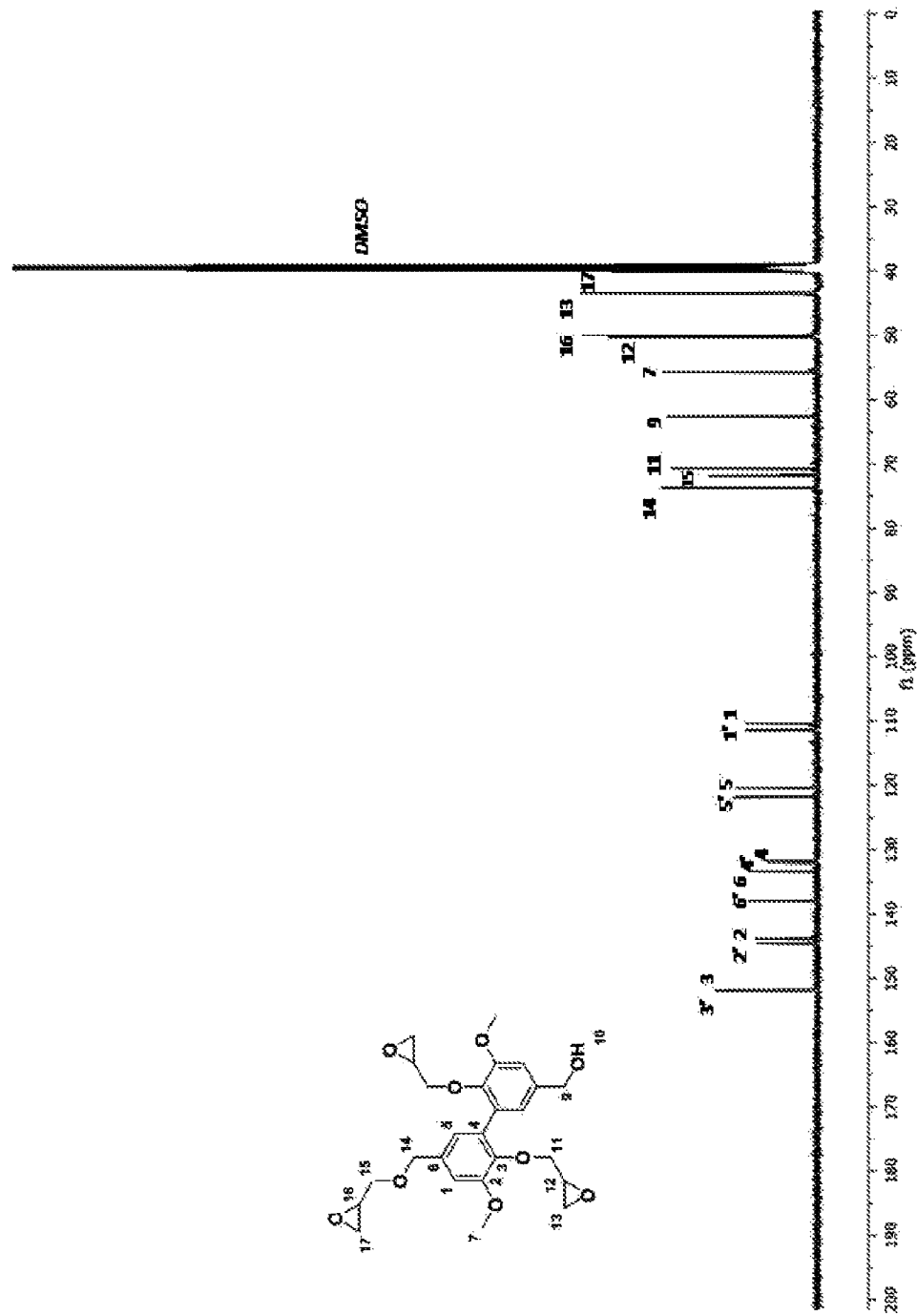

The spectra are shown in FIGS. 8A and 8B respectively.

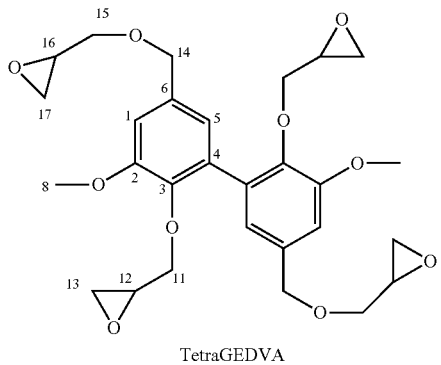 [SMILES: COc1cc(COCC2CO2)cc(-c2cc(COCC3CO3)cc(OC)c2OCC2CO2)c1OCC1CO1 ; "TetraGEDVA"]

TetraGEDVA $^1$H NMR (400 MHz, DMSO-d6, δ (ppm)): δ 7.02 (d, H1), 6.76 (d, H5), 4.50 (s, H14), 3.92 (m, H11), 3.86 (s, H8), 3.76 (m, H11b), 3.70 (m, H15), 3.28 (m, H15b), 3.14 (m, H16), 2.97 (m, H12), 2.73 (m, H17), 2.60 (m, H13), 2.55 (m, H17b), 2.35 (m, H13b).

$^{13}$C NMR (400 MHz, DMSO-d6, δ (ppm)): δ 152.10 (s, C3), 144.51 (s, C2), 133.51 (s, C6), 131.81 (s, C4), 121.83 (s, C5), 111.52 (s, C1), 73.77 (s, C14), 71.90 (s, C15), 63.14 (s, C11), 55.79 (s, C8), 50.30 (s, C12), 50.03 (s, C16), 43.44 (s, C13 C17).

Figure 9A:
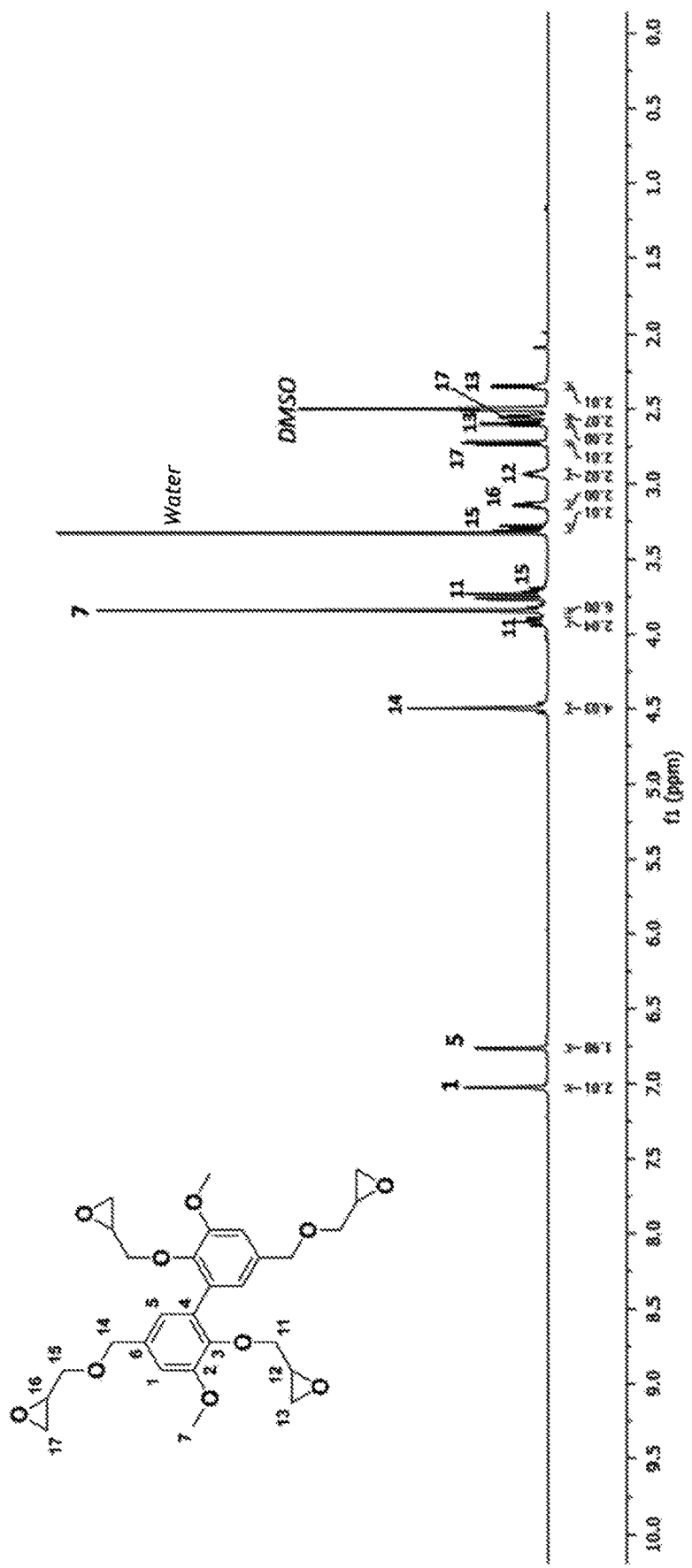
Figure 9B:
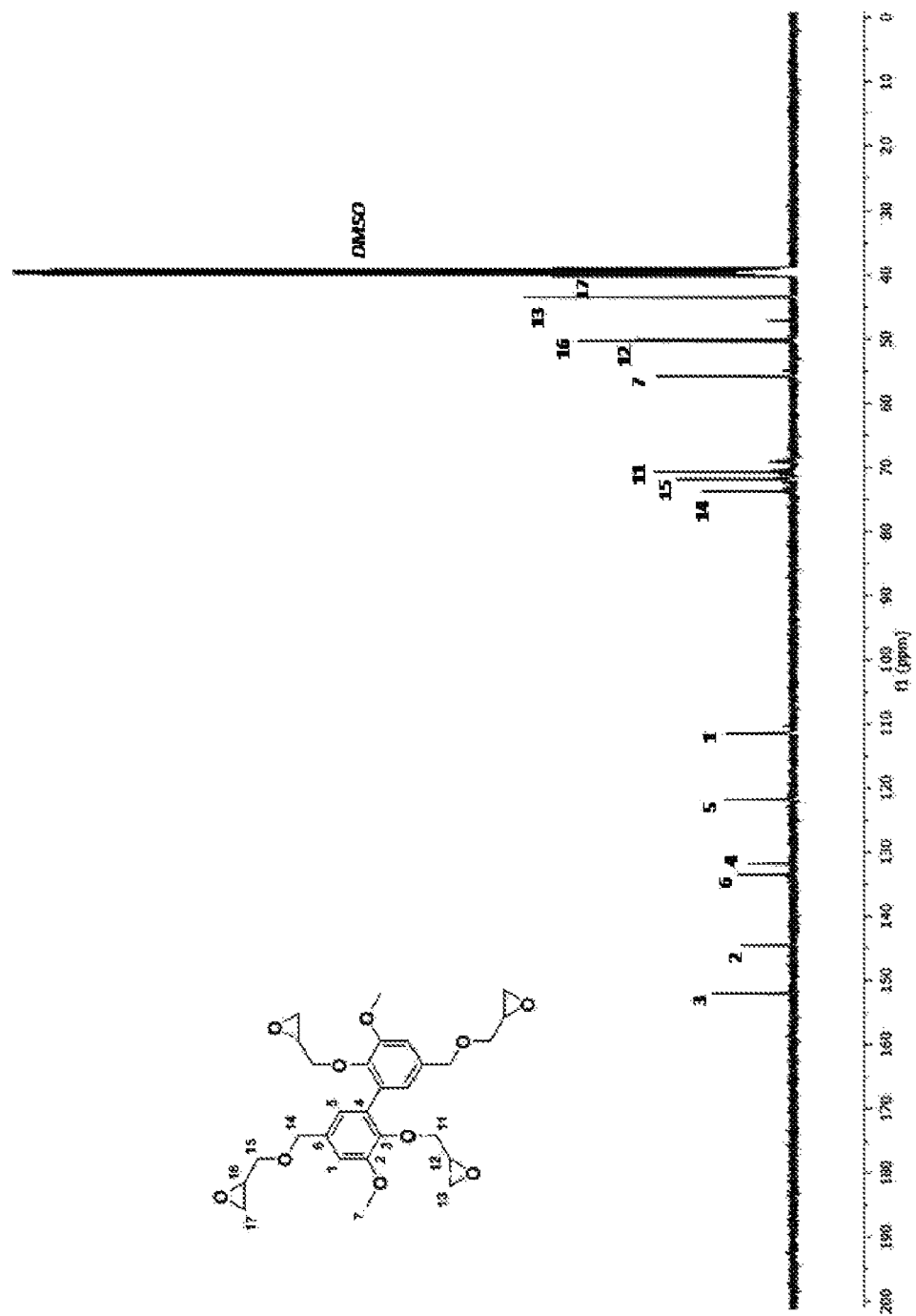

The spectra are shown in FIGS. 9A and 9B respectively.

More specifically, this purification step was carried out on the mixture obtained at the end of step B1 above to isolate the TetraGEDVA (thermosetting epoxy resin) which was tested with different types of hardeners.

The amine type hardeners tested were:
diamino diphenyl sulfone (DDS), marketed by Sigma Aldrich. This conventional hardener has the formula:

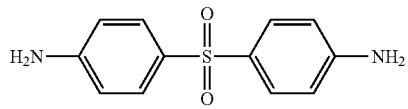

and
3,4-dimethoxydianiline of formula (I) (see Example 2 above).

The hardener was used, for each test, in the stoichiometric ratio: epoxy/amine=2/1. The polyepoxide (epoxy resin+ hardener) was generated, in small quantities (a few mg), during the implementation of differential scanning calorimetry (DSC). Its glass transition temperature (Tg) was thus determined directly.

The rate of residual coke, after degradation at 900° C., determined by thermogravimetric analysis (TGA) (Char900), was determined on this small quantity generated during the DSC analysis. The results are shown in Table 1 below.

TABLE 1

| Properties | DGEBA/DDS | DGEBA/mDVAn | TetraGEDVA/mDVAn |
|---|---|---|---|
| Tg (° C.) | 204 | 176 | 212 |
| Char900 (%) | 18 | 28 | 48 |

The figures in this table confirm the interest of the compounds of the invention.

The invention claimed is:
1. A difunctional biphenyl compound having the formula (I):

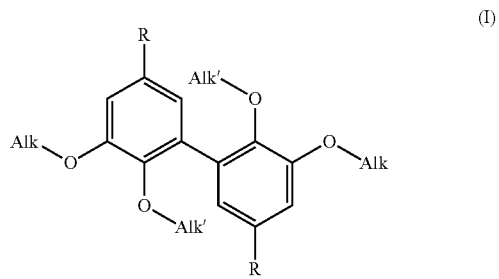

wherein:
Alk is a linear or branched alkyl group having from 1 to 6 carbon atoms,
Alk' is a linear or branched alkyl group having from 1 to 6 carbon atoms, and
R is selected from —CH$_2$—NH$_2$, —N═C═O and —NH$_2$;
it being understood that the compound of formula (I) is not 3,4-dimethoxydianiline.

2. The biphenyl compound as claimed in claim 1, of formula (I) wherein Alk is a methyl group.

3. The biphenyl compound as claimed in claim 1, of formula (I) wherein Alk' is a methyl group.

4. The biphenyl compound as claimed in claim 1, which consists of is:
3,4-dimethoxydivanyllylamine, or
3,4-dimethoxydiphenylisocyanate.

5. A process for preparing a compound of formula (I):

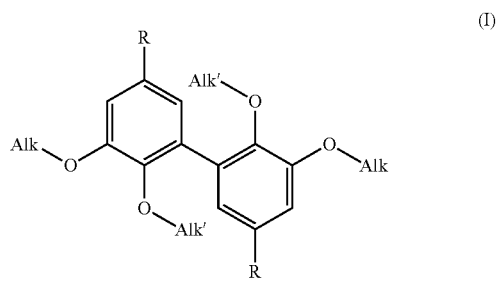

wherein:
Alk is a linear or branched alkyl group having from 1 to 6 carbon atoms,
Alk' is a linear or branched alkyl group having from 1 to 6 carbon atoms, and
R is selected from —CH$_2$—NH$_2$, —N═C═O and —NH$_2$;
which process comprises:
a) providing a product selected from the group consisting of vanillin, analogues of vanillin having an —O—(C$_2$-C$_6$)alkyl group in the 3-position, esters of vanillin and analogues of said esters having an —O—($C_2$-$C_6$)alkyl group in the 3-position;

b) dimerizing said product to obtain a dimer, c) treating said dimer obtained to convert its phenolic —OH functions to —OAlk' alkoxy functions and either its aldehyde functions to aminomethyl functions (—$CH_2$—$NH_2$) or its ester functions to isocyanate (—N=C=O) or amino (—$NH_2$) functions.

6. The process as claimed in claim 5, wherein the product selected in step a) is vanillin of natural origin or a vanillin ester obtained from vanillin of natural origin.

7. The process as claimed in claim 5, wherein the product selected in step a) is vanillin or a vanillin analogue having an O—($C_2$-$C_6$)alkyl group in the 3-position, and wherein step c) comprises c1) either alkylating the phenolic —OH functions of the dimer obtained in step b) then converting the aldehyde functions of said alkylated dimer to oxime functions, or converting the aldehyde functions of said dimer to oxime functions then alkylating the phenolic —OH functions of said dimer with oxime functions, in order to obtain an alkylated divanillyl oxime; and c2) reducing said alkylated divanillyl oxime to obtain an alkylated divanillyl amine having the formula (I) wherein R=—$CH_2$—$NH_2$.

8. The process as claimed in claim 5, wherein the product selected in step a) is a vanillin ester or an analogue of said ester having an —O—($C_2$-$C_6$)alkyl group in the 3-position;

and wherein step c) comprises c1) either saponifying the dimer obtained in step b) to obtain a divanillic acid and alkylating the phenolic —OH functions of said divanillic acid, or alkylating the phenolic —OH functions of said dimer to obtain an alkylated divanillyl ester and saponifying said alkylated divanillyl ester, to obtain an alkylated divanillic acid;

c2) acylating said alkylated divanillic acid to obtain an alkylated acyl diazide;

c3) carrying out a Curtius rearrangement on said alkylated acyl diazide to obtain a dialkoxydiphenyl isocyanate having the formula (I) wherein R=—N=C=O; and c4) optionally, hydrolyzing said dialkoxydiphenyl isocyanate to obtain an alkylated dianiline of formula (I) wherein R=—$NH_2$.

9. A method of obtaining a thermoset resin, which comprises reacting a thermosetting resin with a compound of formula (I):

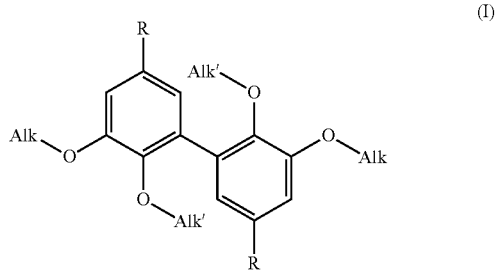

wherein:
Alk is a linear or branched alkyl group having from 1 to 6 carbon atoms,
Alk' is a linear or branched alkyl group having from 1 to 6 carbon atoms, and
R is selected from —$CH_2$—$NH_2$, —N=C=O and —$NH_2$.

10. The method as claimed in claim 9, wherein in formula (I) Alk is a methyl group.

11. The method as claimed in claim 9, wherein in formula (I) Alk' is a methyl group.

12. The method as claimed in claim 9, wherein the compound of formula (I) is 3,4-dimethoxydivanyllylamine, 3,4-dimethoxydianiline or 3,4-dimethoxydiphenylisocyanate.

13. The method as claimed in claim 9, wherein the thermosetting resin is selected from the group consisting of epoxy resins, polycarbonate resins, polycarboxylic acid resins, polyol resins and polyamide resins.

14. The method as claimed in claim 13, wherein in formula (I) R=—$CH_2$—$NH_2$ or —$NH_2$ and wherein the thermosetting resin is an epoxy resin containing at least one polyepoxide biphenyl compound selected from the group consisting of:
diglycidyl ether of bisphenol, monomer or oligomer,
diglycidyl ether of divanillyl alcohol (DiGEDVA),
triglycidyl ether of divanillyl alcohol (TriGEDVA),
tetraglycidyl ether of divanillyl alcohol (TetraGEDVA), and
mixtures of at least two of said glycidyl ethers of divanillyl alcohol.

15. A thermoset resin obtained by the method of claim 9.

16. A thermoset resin obtained by the method of claim 14.

* * * * *

UNITED STATES PATENT AND TRADEMARK OFFICE
CERTIFICATE OF CORRECTION

| | |
|---|---|
| PATENT NO. | : 11,384,195 B2 |
| APPLICATION NO. | : 16/968474 |
| DATED | : July 12, 2022 |
| INVENTOR(S) | : Etienne Savonnet et al. |

It is certified that error appears in the above-identified patent and that said Letters Patent is hereby corrected as shown below:

In the Claims

In Claim 4 (at Column 28, Line 37), should read:
The biphenyl compound as claimed in claim 1, which is:
- 3,4-dimethoxydivanyllylamine, or
- 3,4-dimethoxydiphenylisocyanate.

Signed and Sealed this
Sixteenth Day of August, 2022

Katherine Kelly Vidal
*Director of the United States Patent and Trademark Office*